(12) United States Patent
Lin

(10) Patent No.: US 7,332,647 B2
(45) Date of Patent: Feb. 19, 2008

(54) FISH PRODUCED BY NUCLEAR TRANSFER FROM CULTURED CELLS

(75) Inventor: Shuo Lin, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 43 days.

(21) Appl. No.: 10/517,880

(22) PCT Filed: Jun. 11, 2003

(86) PCT No.: PCT/US03/18393

§ 371 (c)(1),
(2), (4) Date: Dec. 13, 2004

(87) PCT Pub. No.: WO03/103378

PCT Pub. Date: Dec. 18, 2003

(65) Prior Publication Data

US 2005/0177889 A1  Aug. 11, 2005

Related U.S. Application Data

(60) Provisional application No. 60/387,678, filed on Jun. 11, 2002.

(51) Int. Cl.
*A01K 67/027* (2006.01)
*C12N 15/00* (2006.01)
(52) U.S. Cl. .................................... 800/20; 800/24
(58) Field of Classification Search ............... None
See application file for complete search history.

(56) References Cited

U.S. PATENT DOCUMENTS

2002/0178461 A1  11/2002  Lin

OTHER PUBLICATIONS

McCreath, KJ et al. 2000, Production of gene-targeted sheep by nuclear transfer from cultured somatic cells, Nature, 405, 1066-1069.*
Kono, T. 1997, Nuclear transfer and reprogramming, Reviews of Reproduction, 2:74-80.*
Fulka, J et al., 1998, Cloning by somatic cell nuclear transfer, Bioessays, 20:847-851.*
Denning, C. 2001, Nature Biotechnology, vol. 19, pp. 559-562.*
Long, Q et al, 1997, Development, 124:4105-4111.*
Kawakami, K et al., 2000, Proviral insertions in the zebrafish hagoromo gene, encoding an F-box/WD40-repeat protein, cause stripe pattern anomalies, Current BIology, 10:463-466.*
Murphey and Zon ,2002, Nature Biotechnology, 20:785-786.*
Chen et al, 2002, Aquaculture, 214:67-79.*
"Production of zebrafish germ-line chimeras from embryo cell cultures," Ma et al., PNAS, Feb. 27, 2001, vol. 98, No. 5, 2461-2466.
"Embryonic and genetic manipulation in fish," Zhu et al., Cell Research (2000), 10, 17-27.
"Studies on the developmental potentiality of cultured cell nuclei of fish," Hongxi et al., Acta Hydrobiologica Sinica, Mar. 1986, vol. 10, No. 1, 1-10, abstract only.
"Development and gene expression of nuclear transplants generated by transplantation of cultured cell nuclei into non-enucleated eggs in the medaka *Oryzias latipes*," Ju et al., Develop. Growth Differ. (2003) 45, 167-174.
"Transplantation of blastula nuclei to non-enucleated eggs in the medaka, *Oryzias latipes*," Niwa et al., Develop. Growth Differ. (1999) 41, 163-172.
"Cloned zebrafish by nuclear transfer from long-term-cultured cells," Lee et al., http://www.biotech.nature.com, Aug. 2002, vol. 20, Nature Biotechnology, 795-799.
"Nuclear transplantation of somatic cells of transgenic red carp," Zhao et al., Acta Genetica Sinica, May 2002, 406-412.
"Fertile and diploid nuclear transplants derived from embryonic cells of a small laboratory fish, medaka (*Oryzias latipes*)," Wakamatsu et al., PNAS, Jan. 30, 2001, vol. 98, No. 3, 1071-1076.
"Studies on factors affecting the development of embryos from somatic cell nuclear transplantation in the fish," Liu et al., Zoological Research, Apr. 2002 (2): 107-112.
"Human factor IX transgenic sheep produced by transfer of nuclei from transfected fetal fibroblasts," Schnieke et al., Science, vol. 278, Dec. 19, 1997, 2130-2133.
"Factors affecting the efficiency of somatic cell nuclear transplantation in the fish embryo," Liu et al., Jounal of Experimental Zoology, 293:719-725 (2002), 719-725.
"Animal cloning—the route to new genomics in agriculture and medicine," DiBerardino, Differentiation (2001) 68:67-83.

* cited by examiner

*Primary Examiner*—Valarie Bertoglio
(74) *Attorney, Agent, or Firm*—Gates & Cooper LLP

(57) ABSTRACT

The disclosure provided herein teaches that fertile transgenic fish can be generated by nuclear transfer using cultured cells as embryonic fibroblasts.

14 Claims, 9 Drawing Sheets

FIG. 7

| Clones | Genomic Seq. | LTR | Proviral Seq. |
|---|---|---|---|
| Trap1 | ATGTAACTAA | ACTTTCTGGGGTGG | ACATCC |
| Trap11 | GTGAACCATT | ACTTTCTGGGGTGG | ACATCC |
| Trap19 | GGAGAGTTTC | ACTTTCTGGGGTGG | ACATCC |
| Trap31 | CTAACTACNG | ACTTTCTGGGGTGG | ACATCC |
| Trap36 | ATATATTTCAG | ACTTTCTGGGGTGG | ACATCC |
| TrapA3 | GATTTGTGAT | ACTTTCTGGGGTGG | ACATCC |
| TrapA4 | ATAGAAACGG | ACTTTCTGGGGTGG | ACATCC |

SEQUENCE LISTING

<160> NUMBER OF SEQ ID NOS: 7

<210> SEQ ID NO 1
<211> LENGTH: 30
<212> TYPE: DNA
<213> ORGANISM: Danio rerio

<400> SEQUENCE: 1
atgtaactaa actttctggg gtggacatcc                                30

<210> SEQ ID NO 2
<211> LENGTH: 30
<212> TYPE: DNA
<213> ORGANISM: Danio rerio

<400> SEQUENCE: 2
gtgaaccatt actttctggg gtggacatcc                                30

<210> SEQ ID NO 3
<211> LENGTH: 30
<212> TYPE: DNA
<213> ORGANISM: Danio rerio

<400> SEQUENCE: 3
ggagagtttc actttctggg gtggacatcc                                30

<210> SEQ ID NO 4
<211> LENGTH: 30
<212> TYPE: DNA
<213> ORGANISM: Danio rerio
<220> FEATURE:
<221> NAME/KEY: misc_feature
<222> LOCATION: (9)...(9)
<223> OTHER INFORMATION: n = a, t, c, or g

<400> SEQUENCE: 4
ctaactacng actttctggg gtggacatcc                                30

<210> SEQ ID NO 5
<211> LENGTH: 31
<212> TYPE: DNA
<213> ORGANISM: Danio rerio

<400> SEQUENCE: 5
atatatttca gactttctgg ggtggacatc c                              31

<210> SEQ ID NO 6
<211> LENGTH: 30
<212> TYPE: DNA
<213> ORGANISM: Danio rerio

<400> SEQUENCE: 6
gatttgtgat actttctggg gtggacatcc                                30

<210> SEQ ID NO 7
<211> LENGTH: 30
<212> TYPE: DNA
<213> ORGANISM: Danio rerio

<400> SEQUENCE: 7
atagaaacgg actttctggg gtggacatcc                                30

FISH PRODUCED BY NUCLEAR TRANSFER FROM CULTURED CELLS

RELATED APPLICATIONS

This application claims priority under Section 119(c) from U.S. Provisional Application Ser. No. 60/387,678 filed Jun. 11, 2002, the contents of which are incorporated herein by reference.

STATEMENT OF GOVERNMENT SUPPORT

This invention was made with Government support by a National Institutes of Health Grant R01 RR13227. The Government may have certain rights in this invention.

FIELD OF THE INVENTION

The present invention relates to methods for generating transgenic piscine species such as Danio rerio from cultured cells as well as fish generated by such methods.

BACKGROUND OF THE INVENTION

Zebrafish has become an important organism for the study of vertebrate development due to its accessibility to forward genetics, embryonic manipulation and transgenic analysis (see, e.g. Amsterdam, A et al, Genes Dev 13, 2713-24 (1999); Long, Q et al., Development 124, 4105-11 (1997); Haffter, P et al., Development 123, 1-36 (1996); Solnica-Krezel, L et al., Development 123, 67-80 (1996)). Methods are available to perform large-scale mutagenesis screens, allowing identification of key regulatory genes in development. In addition, transparent zebrafish embryos are well suited for manipulations involving DNA or mRNA injection, cell labeling, and transplantation. Nevertheless, to fully realize the potential of this organism, tools of reverse genetics are needed. Once the scheduled zebrafish genome project is complete, targeted genetic manipulations will become even more desirable for zebrafish. Although zebrafish cell cultures exhibiting some characteristics of embryonic stem cells have been described, such short-term cell cultures do not provide adequate time for genetic manipulation such as gene knockouts (see, e.g. Ma et al., Proc Natl Acad Sci USA 98, 2461-6 (2001)).

As an alternative to embryonic stem cells, production of cloned animal using cultured cells offers the possibility of targeted genetic manipulations (see, e.g. Lai, L et al., Science 295, 1089-92 (2002); McCreath, K J et al., Nature 405, 1066-9 (2000)). Nuclear transfer has been in progress for approximately 50 years since its first demonstration in frogs (see, e.g. Briggs, R & King, T J Proc Natl Acad Sci USA 38, 455-63 (1952)). Since then, amphibians have been commonly used for studying nuclear transfer. However, subsequent reports with differentiated somatic cells did not produce individuals that could survive beyond the tadpole stage (see, e.g. Gurdon, J B Adv Exp Med Biol 62, 35-44 (1975); Wabl et al., Science 190, 1310-2 (1975); Di Berardino et al., Differentiation 50, 1-13 (1992); Orr et al., Proc Natl Acad Sci USA 83, 1369-73 (1986)). Similar attempts were made to produce cloned animals in cattle, sheep, rabbit, and pig for commercial benefits (see, e.g. Prather et al., Biol Reprod 37, 859-66 (1987); Willadsen, S M Nuclear transplantation in sheep embryos Nature 320, 63-5 (1986); Stice, S L & Robl, J M Biol Reprod 39, 657-64 (1988); Prather et al., Biol Reprod 41, 414-8 (1989)). After the birth of Dolly the sheep from differentiated cells (see, e.g. Wilmut et al., Nature 385, 810-3 (1997)), a number of successful animal cloning experiments using somatic cells have been achieved, including recent reports producing "gene-knockout" sheep and pigs by nuclear transfer from genetically manipulated somatic cells (see, e.g. Lai, L et al., Science 295, 1089-92 (2002); McCreath, K J et al., Nature 405, 1066-9 (2000)).

Nuclear transfer in fish has been studied since the 1960's. Gasaryan et al. transplanted uncultured blastula nuclei into non-enucleated and enucleated eggs of the loach and obtained feeding larvae (see, e.g. Gasaryan et al., Nature 280, 585-7 (1979)). Fish nuclei of blastula cells from different genera were transplanted into enucleated eggs to study nucleo-cytoplasmic interaction (see, e.g. Zhu, Z Y & Sun, Y H Cell Res 10, 17-27 (2000)). Recently, Wakamatsu et al. demonstrated that diploid and fertile medaka could be produced by nuclear transfer using blastula cells as donors (see, e.g. Wakamatsu, Y Proc Natl Acad Sci USA 98, 1071-6 (2001)). These findings show that nuclei prepared from fresh blastula cells can be reprogrammed in fish to support embryonic and adult development.

In existing technologies involving fish, donor cells typically non-cultured blastula cells that have very limited potential for in vitro genetic manipulation. Consequently there is a need in the art for methods that overcome the limitations associated with the existing technologies. The methods disclosed herein satisfy this need. This disclosure therefore provides a significant advancement in technologies involving the targeted genetic manipulation of fish.

SUMMARY OF THE INVENTION

The disclosure provided herein teaches that fertile transgenic fish can be obtained by nuclear transfer using cultured cells derived from a progenitor fish. For example, the disclosure provided herein teaches the successful cloning of diploid fish from cultured embryonic fibroblasts derived from fish embryos. The use of such cultured cells provides significant advantages in a variety of methods, particularly those that involve the introduction of exogenous nucleic acid sequences into the genome of cells (e.g. via a targeting vector such as a retrovirus); and the selection cells possessing the targeted insertion. In an illustrative embodiment of the invention, zebrafish embryonic fibroblast donor nuclei were modified by retroviral insertions expressing the green fluorescent protein (GFP) and then transplanted into manually enucleated zebrafish eggs. These nuclear transplants produced fertile and diploid offspring and their $F_1/F_2$ progeny continued to express GFP in a pattern identical to that of the founder fish. This finding demonstrates that slow dividing nuclei from cultured cells can be reprogrammed to support rapid embryonic development and provides a foundation for targeted genetic manipulations in fish.

The invention disclosed herein has a number of embodiments. A preferred embodiment of the invention is a method of making a transgenic fish comprising the steps of introducing an exogenous nucleic acid sequence into the genome of a cultured cell derived from a progenitor fish, transplanting the nucleus of this cell into an enucleated egg derived from a parental fish; and then placing the egg generated by this step into conditions suitable for embryonic fish development so that a transgenic fish develops and then hatches. In one preferred embodiment of the invention, the transgenic fish is fertile. In another preferred embodiment of the invention, the transgenic fish has a diploid number of chromosomes.

In a specific embodiment of this method, the exogenous nucleic acid sequence that is used to generate the transgenic fish includes a gene such as a marker protein that is then expressed in the transgenic fish. In another embodiment of the invention, the exogenous nucleic acid comprises a fragment of DNA coding for a reporter or selectable marker gene such as those used in gene-trapping methodologies. Alternatively, the transgenic fish is a knock-out transgenic animal having at least one endogenous gene product that is inactivated by the exogenous nucleic acid sequence.

In highly preferred embodiments of the invention, the cultured cell used to generate the transgenic fish is a fibroblast derived from an embryo of the progenitor fish. As disclosed herein, fish have been generated from cells in such cultures that have been passaged for more than six months. Preferably the embryonic fibroblast cell that is derived from the progenitor fish has been maintained in cell culture for an amount of time sufficient for at least 10, 20, 30, 40, 50, 60, 70, 80, 90, 100, 110, 120, 130, 140, 150, 160, 170 or 180 cell divisions. Optionally, the cultured cell derived from the progenitor fish has been frozen prior to the introduction of the exogenous nucleic acid sequence into its genome and/or prior to transplanting the nucleus of this cell into an enucleated egg derived from a parental fish.

Another highly preferred embodiment of the invention is a transgenic fish made according to these methods.

Yet another embodiment of the invention is a method of making a progeny fish comprising obtaining a cell from a progenitor fish, maintaining the cell in culture an amount of time sufficient to introduce an exogenous nucleic acid sequence into the genome of the cell and to then identify the cell containing the an exogenous nucleic acid sequence within a plurality of cells comprising the cell having the exogenous nucleic acid sequence and a cell lacking the exogenous nucleic acid sequence, transplanting the nucleus of this cell into an enucleated egg from a parental fish, and then placing the egg generated by this transplantation step into conditions suitable for embryonic fish development so that the progeny fish develops and then hatches. In a preferred embodiment of the invention, the progeny fish that is generated by this method is fertile. In another preferred embodiment of the invention, the progeny fish has a diploid number of chromosomes.

In preferred embodiments of this method, the progeny fish is a transgenic fish. In one embodiment of this method, an exogenous nucleic acid sequence that is used to generate the transgenic fish includes a gene such as a marker protein that is then expressed in the transgenic fish. In another embodiment of the invention, the exogenous nucleic acid that is used to generate the transgenic fish comprises a sequence that regulates gene expression such as the promoter and/or enhancer elements. Alternatively, the transgenic fish is a knock-out transgenic animal having at least one endogenous gene product that is inactivated by the exogenous nucleic acid sequence that is used to generate the transgenic fish.

In highly preferred embodiments of the invention, the cultured cell used to generate the progeny fish is a fibroblast derived from the embryo of the progenitor fish. As disclosed herein, fish have been generated from cells in such cultures that have been passaged for more than six months. Preferably this embryonic fibroblast cell that is derived from the progenitor fish has been maintained in cell culture for an amount of time sufficient for at least 10, 20, 30, 40, 50, 60, 70, 80, 90, 100, 110, 120, 130, 140, 150, 160, 170 or 180 cell divisions. Optionally, the cultured cell derived from the progenitor fish has been frozen prior to the introduction of the exogenous nucleic acid sequence into its genome and/or prior to transplanting the nucleus of this cell into an enucleated egg derived from a parental fish.

Another highly preferred embodiment of the invention is a progeny fish made according to these methods.

The methods disclosed herein are applicable to the variety of fish species that have been shown to be amenable to nuclear transplantation. Preferably the progenitor fish are of the species *Danio rerio, Oryzias latipes, Misgurnus fossilis, Salmo irdeus, Salmo salar, Oreochromis nilotica, Parasilurus asoltus, Mylopharyngodon poceus, Ctnopharyngodon idellus, Hypophthalmichihys molivrix, Aristichthys nobilis, Cyprinus Carpio* or *Carassius aurantus*. Most preferably the progenitor fish are of the species *Danio rerio*.

BRIEF DESCRIPTION OF THE FIGURES

FIG. 7 shows the junction sequences of isolated proviral insertions by Neo-TP. Sequences in red are retrovirus sequences and in black are cellular DNA sequences. The clones refer to the following sequences; Trap1 (SEQ ID: 1); Trap11 (SEQ ID: 2); Trap19 (SEQ ID: 3); Trap31 (SEQ ID: 4); Trap36 (SEQ ID: 5); TrapA3 (SEQ ID: 6); and TrapA4 (SEQ ID: 7).

DETAILED DESCRIPTION OF THE INVENTION

Figure 1:
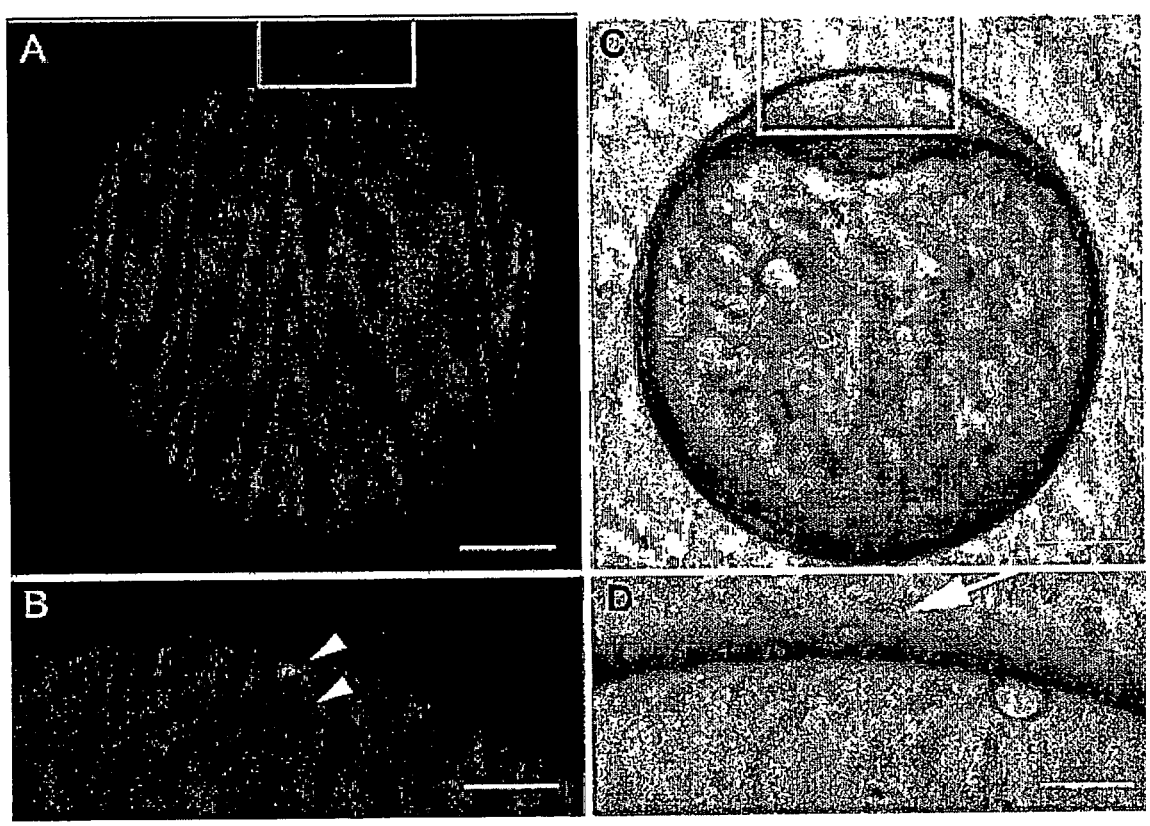
FIG. 1 illustrates zebrafish recipient eggs used for nuclear transfer. (a) Hoechst 33342 staining of an unfertilized egg. (b) Inset from (a) showing both nucleus and polar body (arrowheads). The egg nucleus is located just underneath the egg surface against the polar body. (c) Bright field view of an unfertilized egg. (d) Inset from (c) showing the second polar body (arrow). Scale bars: a and c=150 µm. b and d=50 µm.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., 1989, Molecular Cloning: A Laboratory Manual, 2d ed., Cold Spring Harbor Laboratory Press, Cold Spring Harbor, N.Y. and Ausubel et al., Current Protocols in Molecular Biology, Wiley Interscience Publishers, (1995) as well as text describing the culture of fish such as Westerfield, M. (2000), "The Zebrafish Book", A guide for the laboratory use of zebrafish (*Danio rerio*). 4th ed., Univ. of Oregon Press, Eugene and related texts such as Marie A. Di Berardino "Genomic Potential of Differentiated Cells" (1997) Columbia University Press. As appropriate, procedures involving the use of commercially available kits and reagents are generally carried out in accordance with manufacturer defined protocols and/or parameters unless otherwise noted.

A. Technology of the Invention

The disclosure provided herein relates to methods of making transgenic fish from cultured cells, methods of generating fish progeny from cultured cells and the fish generated by such methods. Also disclosed are methods of using such transgenic fish and fish progeny. For example, as discussed in detail below, fertile transgenic fish can be obtained by nuclear transfer using cultured embryonic fibroblast cells that have been modified to incorporate a transgene of interest. These nuclear transplants produced fertile and diploid offspring and their $F_1/F_2$ progeny continued to express the transgene in a pattern identical to that of the founder fish. This finding demonstrates that slow dividing nuclei from cultured cells can be reprogrammed to support rapid embryonic development and sets up a foundation for targeted genetic manipulations in fish.

The fish disclosed herein allow the study of a wide variety of phenomena including developmental processes, the relationship of cell lineages, the assessment of the effect of specific genes and compounds on the development or maintenance of specific tissues or cell lineages, and the maintenance of lines of fish bearing mutant genes. The transgenic fish disclosed herein are typically characterized by having a genome which contains an exogenous nucleic acid sequence that has been introduced into the fish or a progenitor of the fish (e.g. a retroviral construct encoding a transgene of interest).

As used herein, transgenic fish refers to fish, or progeny of a fish having a genome into which an exogenous nucleic acid sequence has been introduced. As used herein, an exogenous construct is a vector (e.g. plasmid or a retroviral vector) that includes a nudeic acid sequence that is artificially introduced, or was originally artificially introduced, into an animal The term artificial introduction is intended to exclude introduction of a construct through normal reproduction or genetic crosses. That is, the original introduction of a gene or trait into a line or strain of animal by cross breeding is intended to be excluded. A fish into which a construct has been introduced includes fish which have developed from embryonic cells into which the construct has been introduced.

Fish having a genome that includes such constructs that are generated by normal breeding methods from a parental fish having an artificially introduced construct are also considered to contain an exogenous construct. Such fish are progeny of fish into which the exogenous construct has been introduced. As used herein, progeny of a fish are any fish which descend from the fish by sexual reproduction or cloning, and from which genetic material has been inherited. In this context, cloning refers to production of a genetically identical fish from DNA, a cell, or cells of the fish. The fish from which another fish is descended is referred to as a progenitor fish. As used herein, embryonic development of a fish from a cell or cells (embryonic cells, for example), or embryonic development of a cell or cells into a fish, refers to the developmental process by which fertilized egg cells or embryonic cells (and their progeny) grow, divide, and differentiate to form an adult fish.

A transgene or transgenic construct consists of one or more exogenous nucleic acid sequences that are introduced into the genome of a fish to produce a transgenic fish. A transgene construct can be made up of any one of a wide variety of nucleic acid sequences. In one embodiment of the transgenic fish disclosed herein, the transgenic constructs comprise a sequence encoding an expression product such as the green fluorescent protein discussed in the example below. In another embodiment of the invention, the transgenic constructs combine expression sequences operably linked to a sequence encoding an expression product In another embodiment of the invention, the transgenic constructs contain a nucleic acid sequence that is used to construct a "knock out" fish that has a defective or altered gene as a result of homologous recombination between a endogenous gene and the transgene construct. In yet another anther embodiment of the invention, the transgene constructs comprise a nucleic acid sequence that can be used in gene-trapping methodologies. Typically such gene-trapping methodologies involve random insertional mutagenesis using a transgenic construct having a fragment of DNA coding for a reporter or selectable marker gene as a mutagen (see, e.g. Friedrich, G., and Soriano, P. (1993), Methods Enzymol 225, 681-701).

The transgenic constructs of the invention preferably include other components that aid expression, stability or integration of the construct into the genome of a fish. As used herein, components of a transgene construct referred to as being operably linked or operatively linked refer to components being so connected as to allow them to function together for their intended purpose. For example, a promoter and a coding region are operably linked if the promoter can function to result in transcription of the coding region.

Expression sequences are used in the disclosed transgene constructs to mediate expression of an expression product encoded by the construct. As used herein, expression sequences include promoters, upstream elements, enhancers, and response elements. It is preferred that the expression sequences used in the disclosed constructs be homologous expression sequences. As used herein, in reference to components of transgene constructs used in the disclosed transgenic fish, homologous indicates that the component is native to or derived from the species or type of fish involved. Conversely, heterologous indicates that the component is neither native to nor derived from the species or type of fish involved.

Expression sequences are typically divided into two main classes, promoters and enhancers. A promoter is generally a sequence or sequences of DNA that functions when in a relatively fixed location in regard to the transcription start site. A promoter contains core elements required for basic interaction of RNA polymerase and transcription factors, and may contain upstream elements and response elements. Enhancer generally refers to a sequence of DNA that functions at no fixed distance from the transcription start site and can be in either orientation. Enhancers function to increase transcription from nearby promoters. Enhancers also often contain response elements that mediate the regulation of transcription. Promoters can also contain response elements that mediate the regulation of transcription.

Enhancers often determine the regulation of expression of a gene. This effect has been seen in so-called enhancer trap constructs where introduction of a construct containing a reporter gene operably linked to a promoter is expressed only when the construct inserts into the domain of an enhancer (O'Kane and Gehring, Proc. Natl. Acad. Sci. USA 84:9123-9127 (1987), Allen et al., Nature 333:852-855 (1988), Kothary et al., Nature 335:435-437 (1988), Gossler et al., Science 244:463-465 (1989)). In such cases, the expression of the construct is regulated according to the pattern of the newly associated enhancer. Transgenic constructs having only a minimal promoter can be used in the disclosed transgenic fish to identify enhancers. Preferred enhancers for use in the disclosed transgenic fish are those that mediate tissue- or cell lineage-specific expression. More preferred are homologous enhancers that mediate tissue- or cell lineage-specific expression. Illustrative enhances are enhancers from fish GATA-1 and GATA-2 genes (e.g. Enhance from zebrafish GATA-1 and GATA-2 genes).

For expression of encoded peptides or proteins, a transgene construct typically includes sequences that, when transcribed into RNA, mediate translation of the encoded expression products. Such sequences are generally found in the 5' untranslated region of transcribed RNA. This region corresponds to the region on the construct between the transcription initiation site and the translation initiation site (that is, the initiation codon). The 5' untranslated region of a construct can be derived from the 5' untranslated region normally associated with the promoter used in the construct, the 5' untranslated region normally associated with the sequence encoding the expression product, the 5' untranslated region of a gene unrelated to the promoter or sequence encoding the expression product, or a hybrid of these 5' untranslated regions. Optionally, the 5' untranslated region is homologous to the fish into which the construct is to be introduced.

Transgene constructs for use in the disclosed transgenic fish can encode any desired expression product, including peptides, proteins, and RNA. Expression products can include reporter proteins (for detection and quantitation of expression), and products having a biological effect on cells in which they are expressed (by, for example, adding a new enzymatic activity to the cell, or preventing expression of a gene). Many such expression products are known or can be identified.

As used herein, a reporter protein is any protein that can be specifically detected when expressed. Reporter proteins are useful for detecting or quantitating expression from expression sequences. For example, operatively linking nucleotide sequence encoding a reporter protein to a tissue specific expression sequences allows one to carefullly study lineage development. In such studies, the reporter protein serves as a marker for monitoring developmental processes, such as cell migration. Many reporter proteins are known and have been used for similar purposes in other organisms. These include enzymes, such as β-galactosidase, luciferase, and alkaline phosphatase, that can produce specific detectable products, and proteins that can be directly detected. Virtually any protein can be directly detected by using, for example, specific antibodies to the protein. A preferred reporter protein that can be directly detected is the green fluorescent protein (GFP). GFP, from the jellyfish Aequorea victoria, produces fluorescence upon exposure to ultraviolet light without the addition of a substrate (Chalfie et al., Science 263:802-5 (1994)). Recently, a number of modified GFPs have been created that generate as much as 50-fold greater fluorescence than does wild type GFP under standard conditions (Cormack et al., Gene 173:33-8 (1996); Zolotukhin et al., J. Virol 70:4646-54 (1996)). This level of fluorescence allows the detection of low levels of tissue specific expression in a living transgenic animal.

The use of reporter proteins that, like GFP, are directly detectable without requiring the addition of exogenous factors are preferred for detecting or assessing gene expression during fish (e.g. zebrafish) embryonic development. A transgenic fish embryo, carrying a construct encoding a reporter protein and a tissue-specific expression sequences, can provide a rapid real time in vivo system for analyzing spatial and temporal expression patterns of developmentally regulated genes.

The disclosed transgene constructs preferably include other sequences which improve expression from, or stability of, the construct. Such sequences include for example a polyadenylation signal to ensure that transcripts from a transgene will be processed and transported as mRNA. The identification and use of polyadenylation signals in expression constructs is well established. It is preferred that homologous polyadenylation signals be used in the transgene constructs. It is also known that the presence of introns in primary transcripts can increase expression, possibly by causing the transcript to enter the processing and transport system for mRNA. It is preferred that an intron, if used, be included in the 5' untranslated region or the 3' untranslated region of the transgene transcript It is also preferred that the intron be homologous to the fish used, and more preferably homologous to the expression sequences used (that is, that the intron be from the same gene that some or all of the expression sequences are from). The use and importance of these and other components useful for transgene constructs are discussed in Palmiter et al., Proc. Natl. Acad. Sci. USA 88:478-482 (1991); Sippel et al., "The Regulatory Domain Organization of Eukaryotic Genomes: Implications For Stable Gene Transfer" in Transgenic Animals (Grosveld and Kollias, eds., Academic Press, 1992), pages 1-26; Kollias and Grosveld, "The Study of Gene Regulation in Transgenic Mice" in Transgenic Animals (Grosveld and Kollias, eds, Academic Press, 1992), pages 79-98; and Clark et al., Phil. Trans. R. Soc. Lond. B. 339:225-232 (1993).

The disclosed constructs are preferably integrated into the genome of the fish. However, the disclosed transgene construct can also be constructed as an artificial chromosome. Such articial chromosomes containing more that 200 kb have been used in several organisms. Artificial chromosomes can be used to introduce very large transgene constructs into fish. This technology is useful since it can allow faithful recapitulation of the expression pattern of genes that have regulatory elements that lie many kilobases from coding sequences.

The disclosed constructs and methods can be used with a wide variety of fish species. As used herein, fish refers to any member of the classes collectively referred to as pisces. It is preferred that fish belonging to species and varieties of fish of commercial or scientific interest be used. Such fish include salmon, trout, tuna, halibut, catfish, zebrafish, medaka, carp, tilapia, goldfish, and loach. Illustrative fish species include but are not limited to *Danio rerio, Oryzias latipes, Misgurnus anguillicaudatus, Salmo irdeus, Salmo salar, Oreochromis nilotica, Parasilurus asoltus, Mylopharyngodon poceus, Ctnopharyngodon idellus, Hypophthalmichihys molivrix, Aristichthys nobilis, Cyprinus Carpio* and *Carassius aurantus*.

The most preferred fish for use with the disclosed constructs and methods is zebrafish, *Danio rerio*. Zebrafish are a popular experimental animal because they have many of the advantages of popular invertebrate experimental organisms, and include the additional advantage that they are vertebrates. Another significant advantage of zebrafish for the study of development and cell lineages is that, like Caenorhabditis, they are largely transparent (Kimmel, Trends Genet 5:283-8 (1989)). The generation of thousands of zebrafish mutants (Driever et al., Development 123:37-46 (1996); Haffter et al., Development 123:1-36 (1996)) provides abundant raw material for transgenic study of these animals. General zebrafish care and maintenance is described by Streisinger, Natl. Cancer Inst. Monogr. 65:53-58 (1984).

Zebrafish embryos are easily accessible and nearly transparent. Given these characteristics, a transgenic zebrafish embryo, carrying a construct encoding a reporter protein and tissue-specific expression sequences, can provide a rapid real time in vivo system for analyzing spatial and temporal expression patterns of developmentally regulated genes. In addition, embryonic development of the zebrafish is extremely rapid. In 24 hours an embryo develops rudiments of all the major organs, including a functional heart and circulating blood cells (Kimmel, Trends Genet 5:283-8 (1989)). Other fish with some or all of the same desirable characteristics are also preferred.

The disclosed transgenic fish are produced by introducing a transgene construct into cultured cells of a fish, preferably fibroblastic cells, and most preferably fibroblastic cells derived from a fish embryo (embryonic fibroblast cells). Where the transgene construct is introduced into embryonic fibroblast cells, the transgenic fish is obtained by allowing the embryonic cell or cells to develop into a fish. Introduction of constructs into embryonic fibroblast cells of fish, and subsequent development of the fish, are simplified by the fact that embryos develop outside of the parent fish in most fish species.

The disclosed transgene constructs can be introduced into fibroblastic cells derived from a fish embryo cells using any suitable technique. Many techniques for such introduction of exogenous genetic material have been demonstrated in fish and other animals. These include infection with viral vectors (as described in the Examples below), microinjection (described by, for example, Culp et al. (1991)), electroporation (described by, for example, Inoue et al., Cell. Differ. Develop. 29:123-128 (1990); Muller et al., FEBS Lett. 324:27-32 (1993); Murakami et al., J. Biotechnol. 34:35-42 (1994); Muller et al., Mol. Mar. Biol. Biotechnol. 1:276-281 (1992); and Symonds et al., Aquaculture 119:313-327 (1994)), particle gun bombardment (Zelenin et al., FEBS Lett. 287:118-120 (1991)), and the use of liposomes (Szelei et al., Transgenic Res. 3:116-119 (1994)).

Figure 3:
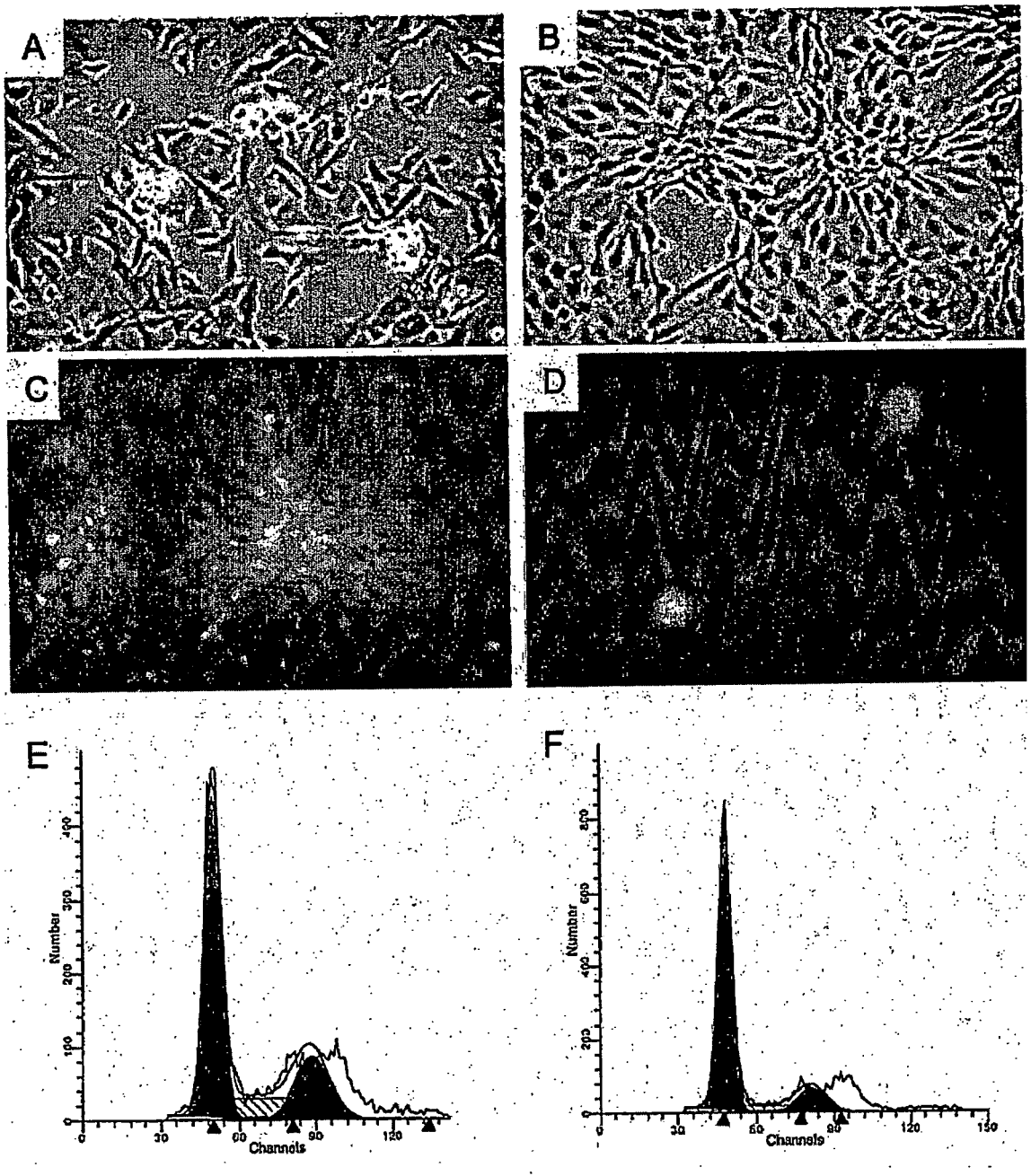
FIG. 3 illustrates a characterization of cultured embryonic fibroblast cells. (a) wild-type primary cells at day 4; (b) bright field of virus-infected cells at 12-week-old; (c) a fluorescence image of cells in (b); (d) individual cells for the nuclear transfer under the fluorescent microscope; (e) FACS histograms of non-starved or (f) 4-day-serum starved cells. Percentage of cells at each cell cycle stage are: (f) G0+G1=58.76%; S=18.52% and G2+M=22.72%. (g) G0+G1=78.59%; S=8.57% and G2+M=12.83%.

Embryos or embryonic cells can generally be obtained by collecting a cell sample from the time of embryonic development encompassing immediately after eggs are laid to immediately before fish hatch. Typically cells are disaggregated from this embryonic sample and placed into in vitro cell culture conditions. Cells from this sample can then be used to obtain a culture of fibroblasts having the characteristics of those shown for example in FIG. 3, typically be simple outgrowth of the fibroblastic population. In a typical method using cells generated in this manner, an exogenous nucleic acid sequence is then introduced into the genome of a embryonic fibroblast cell and the transgenic nucleus of the embryonic fibroblast cell is then transplanted into an enucleated egg cell derived from a parental fish and placed into conditions suitable for embryonic fish development. As is known in the art, this last step generally involves no more than incubating these embryos under the same conditions used for the incubation of eggs. If appropriate, expression of an introduced transgene construct can be observed during development of the embryo.

Fish harboring a transgene can be identified by any suitable means. For example, the genome of potential transgenic fish can be probed for the presence of construct sequences. To identify transgenic fish actually expressing the transgene, the presence of an expression product can be assayed. Several techniques for such identification are known and used for transgenic animals and most can be applied to transgenic fish. Probing of potential or actual transgenic fish for nucleic acid sequences present in or characteristic of a transgene construct is preferably accomplished by Southern or Northern blotting. Also preferred is detection using polymerase chain reaction (PCR) or other sequence-specific nucleic acid amplification techniques.

Identifying the pattern of expression in the disclosed transgenic fish can be accomplished by measuring or identifying expression of the transgene in different tissues (tissue-specific expression), at different times during development (developmentally regulated expression or developmental stage-specific expression), in different cell lineages (cell lineage-specific expression). These assessments can also be combined by, for example, measuring expression (and observing changes, if any) in a cell lineage during development. The nature of the expression product to be detected can have an effect on the suitability of some of these analyses. On one level different tissues of a fish can be dissected and expression can be assayed in the separate tissue samples. Such an assessment can be performed when using almost any expression product This technique is commonly used in transgenic animals and is useful for assessing tissue-specific expression.

This technique can also be used to assess expression during the course of development by assaying for the expression product at different developmental stages. Where detection of the expression product requires fixing of the sample or other treatments that destroy or kill the developing embryo or fish, multiple embryos must be used. This is only practical where the expression pattern in different embryos is expected to be the same or similar. This will be the case when using the disclosed transgenic fish having stable and predictable expression.

A highly preferred way of assessing the pattern of expression of a transgene during development is to use an expression product that can be detected in living embryos and animals. A preferred expression product for this purpose is the green fluorescent protein (GFP). A preferred form of GFP and a preferred technique for measuring the presence of GFP in living fish is described in the examples.

Expression products of the disclosed transgene constructs can be detected using any appropriate method. Many means of detecting expression products are known and can be applied to the detection of expression products in transgenic fish. For example, RNA can be detected using any of numerous nucleic acid detection techniques. The use of reporter proteins as the expression product is preferred since such proteins are selected based on their detectability. The detection of several useful reporter proteins is described in the art (see, e.g. Iyengar et al., Transgenic Res. 1996 May; 5(3):147-66).

Preferred embodiments of the invention use zebrafish. In zebrafish, the nervous system and other organ rudiments appear within 24 hours of fertilization. Since the nearly transparent zebrafish embryo develops outside its mother, the origin and migration of lineage progenitor cells can be monitored by following expression of an expression product in transgenic fish. In addition, the regulation of a specific gene can be studied in these fish. Using zebrafish promoters that drive expression in specific tissues, a number of transgenic zebrafish lines can be generated that express a reporter protein in each of the major tissues including the notochord, the nervous system, the brain, the thymus, and in other tissues. Other important lineages for which specific expression can be obtained include neutral crest, germ cells, liver, gut, and kidney. As discussed in detail below, additional tissue specific transgenic fish can be generated by using gene trap such as "enhancer trap" constructs to identify expression sequences in fish.

For many genes, and especially for genes involved in developmental processes, it would be useful to identify compounds that affect expression of the genes. The disclosed transgenic fish can be exposed to compounds to assess the effect of the compound on the expression of a gene of interest. For example, test compounds can be administered to transgenic fish harboring an exogenous construct containing the expression sequences of a fish gene of interest operably linked to a sequence encoding a reporter protein. By comparing the expression of the reporter protein in fish exposed to a test compound to those that are not exposed, the effect of the compound on the expression of the gene from which the expression sequences are derived can be assessed.

Numerous mutants have been generated and characterized in zebrafish which affect most developmental processes. The disclosed transgenic fish can be used in combination with these and other mutations to assess the effect of a mutant gene on the expression of a gene of interest For example, mutations can be introduced into strains of transgenic fish harboring an exogenous construct containing the expression sequences of a fish gene of interest operably linked to a sequence encoding a reporter protein. By comparing the expression of the reporter protein in fish with a mutation to those without the mutation, the effect of the mutation on the expression of the gene from which the expression sequences are derived can be assessed.

The effect of such mutations on specific developmental processes and on the growth and development of specific cell lineages can also be assessed using the disclosed transgenic fish expressing a reporter protein in specific cell lineages or at specific developmental stages.

Transgene constructs can also be used to genetically mark mutant genes or chromosome regions. For example, in zebrafish, chemical mutagenesis screens have generated more than one thousand different mutants with defects in most developmental processes. If fish carrying a mutation generated in these screens could be more easily identified, a lot of time and labor would be saved. One way to promote rapid identification of fish carrying mutations would be the establishment of balancer chromosomes that carry markers that can be easily identified in living fish. This technology has greatly facilitated the task of identification and maintenance of mutant stocks in Drosophila (Ashburner, Drosophila, A Laboratory Manual (Cold Spring Harbor Laboratory Press, Cold Spring Harbor, N.Y., 1989); Lindsey and Zimm, The Genome of Drosophila melanogaster (Academic Press, San Diego, Calif., 1995)). As used herein, genetically marking a gene or chromosome region refers to genetically linking a reporter gene to the gene or chromosome region. Genetic linkage between two genetic elements (such as genes) refers to the elements being in sufficiently close proximity on a chromosome that they do not segregate from each other at random in genetic crosses. The closer the genetic linkage, the more likely that the two elements will segregate together. For genetic marking, it is preferred that the transgene construct segregate with the gene or chromosomal region of interest more than 60% of the time, it is more preferred that the transgene construct segregate with the gene or chromosomal region of interest more than 70% of the time, it is still more preferred that the transgene construct segregate with the gene or chromosomal region of interest more than 80% of the time, it is still more preferred that the transgene construct segregate with the gene or chromosomal region of interest more than 90% of the time, and it is most preferred that the transgene construct segregate with the gene or chromosomal region of interest more than 95% of the time.

Although it is preferred that mutant genes be genetically marked, any gene of interest or any chromosome region can be marked, and the maintenance and inheritance of the gene can be monitored, in a similar manner. As used herein, an identified mutant gene is a mutant gene that is known or that has been identified, in contrast to a mutant gene which may be present in an organism but which has not been recognized. Genetically mapping of mutant genes or transgenes in fish can be performed using established techniques and the principles of genetic crosses. Generally, mapping involves determining the linkage relationships between genetic elements by assessing whether, and to what extent two or more genetic elements tend to cosegregate in genetic crosses.

Mutant fish in which the mutant gene is marked with an exogenous construct expressing a reporter protein simplify the identification of progeny fish that carry the mutant gene. For example, after a cross, progeny fish can be screened for expression of the reporter protein. Those that express the reporter protein are very likely to have inherited the mutant gene which is genetically linked. Those progeny fish not expressing the reporter protein can be excluded from further analysis.

Transgene constructs can also be used in a variety of gene-trapping constructs such as "enhancer traps" to generate transgenic fish that exhibit tissue-specific expression of an expression product. Transgenic animals carrying enhancer trap constructs often exhibit tissue-specific expression patterns due to the effects of endogenous enhancer elements that lie neat the position of integration. Once it is determined that the exogenous construct is operably linked to an enhancer or other regulatory sequence in a fish, the regulatory element can be isolated by re-cloning the transgene construct. Many general cloning techniques can be used for this purpose. A preferred method of cloning regulatory sequences that have become linked to a transgene construct in a fish is to isolate and cleave genomic DNA from the fish with a restriction enzyme that does not cleave the exogenous construct. The resulting fragments can be cloned in vitro and screened for the presence of characteristic transgene sequences. A search for enhancers in zebrafish using a transgene construct having only a promoter operably linked to a sequence encoding a reporter protein has generated a transgenic line that expresses GFP exclusively in hatching gland cells. A similar procedure can be followed to identify promoters. In this case, a "promoter probe" construct, which lacks any expression sequences, is used. Only if the construct is inserted into the genome downstream of expression sequences will the expression product encoded by the construct be expressed.

The linked genomic sequences of clones identified as containing expression sequences, or any other nucleic acid segment containing expression sequences, can then be characterized to identify potential and actual regulatory sequences. For example, a deletion series of a positive clone can be tested for expression in transgenic fish. Sequences essential for expression, or for a pattern of expression, are identified as those which, when deleted from a construct, no longer support expression or the pattern of expression. The ability to assess the pattern of expression of a transgene in fish using the disclosed transgenic fish and methods makes it possible to identify the elements in the regulatory sequences of a fish gene that are responsible for the pattern of expression. The disclosed transgenic fish, since they can be produced routinely and consistently, allow meaningful comparison of the expression of different deletion constructs in separate fish.

Using cell sorting based on the presence of an expression product, pure populations of cells expressing a transgene construct can be isolated from other cells. Where the transgene construct is expressed in particular cell lineages or tissues, this can allow the purification of cells from that particular lineage. These cells can be used in a variety of in vitro studies. For instance, these pure cell populations can provide mRNA for differential display or subtractive screens for identifying genes expressed in that cell lineage. Progenitor cells of specific tissue could also be isolated. Establishing such cells in tissue culture would allow the growth factor needs of these cells to be determined. Such knowledge could be used to culture non-transgenic forms of the same cells or related cells in other organisms.

Cell sorting is preferably facilitated by using a construct expressing a fluorescent protein or an enzyme producing a fluorescent product. This allows fluorescence activated cell sorting (FACS). A preferred fluorescent protein for this purpose is the green fluorescent protein. The ability to generate transgenic fish expressing GFP in a tissue-and cell lineage-specific manner for different cell types indicates that transgenic fish that express GFP in other types of tissues can be generated in a straightforward manner. The disclosed FACS approach can therefore be used as a general method for isolating pure cell populations from developing embryos based solely on gene expression patterns. This method for isolation of specific cell lineages is preferably performed using constructs linking GFP with the expression sequences of genes identified as being involved in development Numerous such genes have been or can be identified as mutants that affect development. Cells isolated in this manner are useful in transplantation experiments.

B. Use of Zebrafish in Illustrative Embodiments of the Invention

Zebrafish is a superb model organism for cellular and developmental studies. Studies utilizing zebrafish provided a unique opportunity to integrate the tools of forward genetics, experimental embryology and molecular biology towards understanding vertebrate development Zebrafish are used in preferred embodiments of the inventions because adults are small and easy to maintain with females typically producing up to several hundred eggs per mating. Another advantage is that the embryos are transparent and develop outside the mother, allowing access and manipulation of the embryos at very early stages of development. In addition, organ formation can readily be observed from about 12 hours post-fertilization (hpf) under a dissecting microscope. This allows one to quickly screen for defects in embryonic development by simple observation. Lineage-specific progenitor cells can be identified by the expression of tissue-specifc molecular markers or by the green fluorescent protein (GFP) reporter gene under the control of tissue-specific promoters. These qualities offer significant advantages over other vertebrate systems for the study of early events in embryonic development. In addition, zebrafish have become an important model organism for studying development, physiology and diseases. A genome sequencing project is expected to be completed soon to understand the genetic makeup of this model system. The challenge has now shifted to understanding functions of the more than 30,000 predicated genes present in a typical vertebrate genome.

Currently, the ability to create animal models for well-known human genetic diseases as well as to study novel genes revealed by DNA sequencing is severely restrained by the lack of efficient gene knockout technology in zebrafish. The disclosure that zebrafish can be successfully cloned using cultured cells promises an alternative that has been successfully employed in other mammals lacking embryonic stem (ES) cells.

The methods and fish disclosed herein allow artisans to undertake a number of experiments for gene function studies including those involving gene-trap and gene knockout techniques by DNA homologous recombination. Initial gene-trapping studies in these cells have successfully produced cloned zebrafish carrying an expressed gene-trap reporter. DNA homologous recombination may be achieved in cultured cells (e.g. fibroblasts derived from zebrafish embryos) and cells carrying a homologous recombination event may be used to produce normal fertile zebrafish.

The disclosure provided herein allows for a number of important approaches for defining gene functions in zebrafish, e.g. gene-trap and gene knockout approaches. A first approach can be scaled up to trap a large number of zebrafish genes in cultured cells, which can be of different specific lineages to reveal genes required for a particular biological process. A cell library consisting of clones with trapped genes can be established with their individual sequence pre-identified, providing an invaluable resource for gene function studies. For any genes of interest, cloned fish can be further produced from the trapped cells followed by phenotype analysis in vivo. A second approach will provide a technique for the zebrafish community to study their genes of interest in a pre-targeted fashion. The combination of these two approaches will have a profound impact on zebrafish functional genomics, therefore further enhancing the utility of zebrafish as a model system for studying vertebrate development and human diseases. The application of these techniques in the evaluation of a wide variety of physiological processes has been abundantly demonstrated in mice and other mammalian organisms.

Cloning Zebrafish Using Long-term Cultured Cells.

The availability of the ES cells has revolutionized gene function studies in mouse. The ES cells are amenable to various genetic manipulations, such as gene-trapping and homologous recombination, yet are still able to participate in normal embryonic development and contribute to germ line. Taking advantage of the ES cells, it is feasible to create libraries of murine ES cells in which each individual clone has one gene tagged or disrupted. Functions of these genes can then be studied when the cells are used to produce living animals harboring the tagged or disrupted genes. Unfortunately, successful development and utility of ES cells in other animal organisms are yet to be demonstrated.

For nearly 10 years, at least three laboratories have been trying to develop ES cells equivalent to its mouse counterpart in zebrafish (see, e.g. Sun et al., (1995) Mol Mar Biol Biotechnol 4, 193-9) and medaka (see, e.g. Hong et al., (1998) Dev Genes Evol 208, 595-602; Wakamatsu et al., (1994) Mol Mar Biol Biotechnol 3, 185-91). Although these ES-like cells exhibited many characteristics of their mouse counterpart, only short time cultures have been shown to contribute to germ line (see, e.g. Ma et al., (2001) Proc Natl Acad Sci USA 98, 2461-6). It remains unknown whether these cells are still able to contribute to germ line after elongated period of genetic manipulation. With the advances made in the field of nuclear transfer, it has become a reality that, at least in mammals, many cells types including adult somatic cells can be genetically manipulated and their nuclei are still able to promote normal development when transplanted into enucleated eggs (see, e.g. Lai et al., (2002) Science 3, 3; McCreath et al., (2000), Nature 405, 1066-9). This finding offers opportunities to create gene-tagged or "knockout" animals in virtually any organisms in which nuclear transfer can be performed, including zebrafish.

A major breakthrough in zebrafish cloning is disclosed herein (see also, Lee et al., (2002) Nat Biotechnol 20, 795-9). In particular, we demonstrate that fertile zebrafish can be cloned using cultured embryonic fibroblast cells. In demonstrating the success of these methods, we have cloned mote than 15 zebrafish from cultured cells derived from embryos of 5-15 somite stages. In these methods, cells have been cultured for more than 6 months and gone through frozen and thawing processes. Moreover, these cells were infected by retrovirus carrying the GFP market gene and were still able to promote normal development in cloned zebrafish. The cloned adult fish are fertile and continue to produce diploid progeny. Currently, the success rate for zebrafish cloning is about 2%. Considering the fact that zebrafish can produce hundreds of eggs on a weekly basis, this rate generates a sufficient number of cloned fish in a relatively short period of time.

In order to further demonstrate the effectiveness of the techniques disclosed herein, we have expanded our collection of cultured embryonic fibroblast cells. We established additional cell lines using different strains of zebrafish including AB line. The rationale behind generating additional cell types from different zebrafish strains is to generate donor cells that are highly compatible with cytoplasm of recipient eggs from common zebrafish strains. These cells have been frozen at earlier passages (from 6th to 10th) in order to increase their utility for further genetic manipulation such as extended selection periods for DNA homologous recombination.

The methods disclosed herein allows one to perform a wide variety of genetic manipulations to these cells, such as the introduction of exogenous nucleic acid sequences that are used for example to express exogenous gene products (e.g. marker proteins such as GFP), exogenous nucleic acid sequences that are used in gene-trapping studies and exogenous nucleic acid sequences that are used in homologous recombination (e.g. to generate a knock-out transgenic fish having at least one endogenous gene that is inactivated by the exogenous nucleic acid sequence). Such modified cells can then be used for nuclear transfer to test their potential for promoting embryonic and adult development In illustrative examples, gene-trap strategies are use to allow genes to be trapped in cells and then studied in living animals cloned by nuclear transfer. Alternatively, knockout zebrafish can be used to study the various functions of specific genes.

Gene-trapping for Gene Identification and Function Analysis.

Gene-trapping is a method of random insertional mutagenesis that uses a fragment of DNA coding for a reporter or selectable marker gene as a mutagen (see, e.g. Friedrich, G., and Soriano, P. (1993), Methods Enzymol 225, 681-701). Gene-trapping has become a powerful tool for a genome-wide gene discovery and functional analysis in varous model organisms, such as C. elegans (see, e.g. Zwaal et al., (1993), Proc Natl Acad Sci USA 90, 7431-5), Drosophila melanogaster (see, e.g. Spradlng et al., (1999) Genetics 153, 135-77) and mice (see, e.g. Durick et al., (1999) Genome Res 9, 1019-25; Hicks et al., (1997) Nat Genet 16, 338-44). Taking advantage of the ES cells, it is feasible to create libraries of murine ES cells in which each individual clone has one gene tagged, as demonstrated by Zambrowicz et al that more than 2000 genes have been disrupted and sequenced (Zambrowicz et al. (1998) Nature 392, 608-11). Functions of the tagged genes can be analyzed by transplanting ES cells to create a living animal carrying the tagged gene.

In zebrafish, retroviral insertional mutagenesis has been successfuilly developed by direct injection of virus into blastula-stage embryos (see, e.g. Amsterdam et al., (1999) Genes Dev 13, 2713-24; Golling et al., (2002) Nat Genet 31, 135-40). The power of this approach has been demonstrated by the isolation of more than 500 insertional mutants and cloning of 75 mutant genes in a 2-year period. Though many tagged genes can be isolated in short time, creating mutants takes much longer as a mutant can only be analyzed in F3 homozygous fish, which requires more than a year to obtain. Therefore this approach alone is not sufficient to isolate and assign functions to approximately 30,000 genes anticipated in the zebrafish genome. Additionally, the method does not involve pre-selection for gene-traps, an additional step which will improve efficiency for gene identification and functional characterization.

As a complement to the current insertional mutagenesis approach in zebrafish, one can combine the techniques of gene trapping and nuclear transfer. Gene-trap experiments in cultured zebrafish cells can be used to analyze the identity and structure of the trapped genes prior to any further functional studies. With an extensive panel of genes carrying the identified traps, genes of interest to individual investigators can then be used to obtain cloned fish This method should generate heterozygous fish in the F0 generation and homozygous in the F2, so mutant phenotypes can be analyzed earlier. As a demonstration of the applicability of such methods, using two gene-trapping constructs that have been previously adopted in mice, we have obtained positive trapping events in cultured cells, isolated a number of genomic sequences flanking the trapped zebrafish genes/ESTs and also obtained cloned fish carrying gene traps that are actively expressed in cultured cells.

Figure 5A:
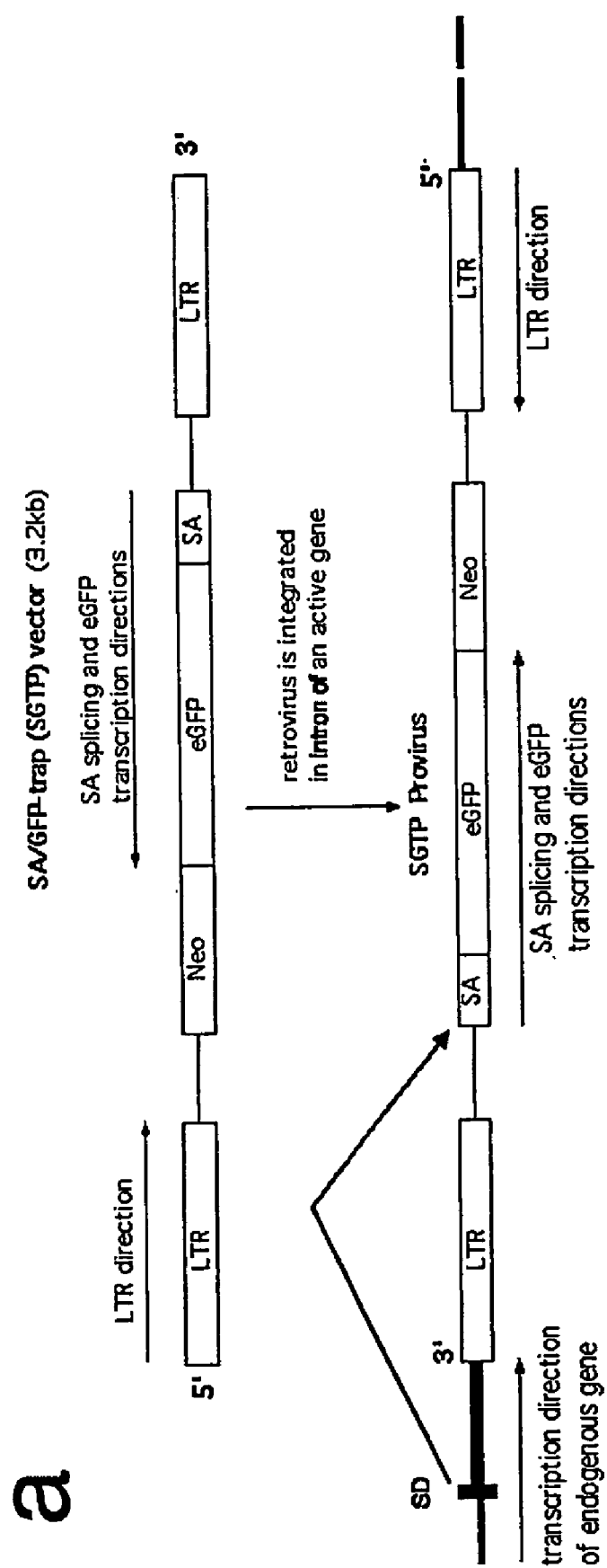
FIG. 5 illustrates a SA/GFP-trap vector and selection of trap-positive cells expressing GFP. (a) SA/GFP-TP retroviral gene-trap construct contains a splicing acceptor (SA) with a partial peptide fused in frame with eGFP. If the vital vector is inserted in an intron and a fusion protein is generated from its upstream coding exon serving as a splicing donor (SD), the eGFP will be expressed. This can be observed under a fluorescent microscope (b) or selected by FACS (c, left trapped cells and tight control).
Figure 6A:
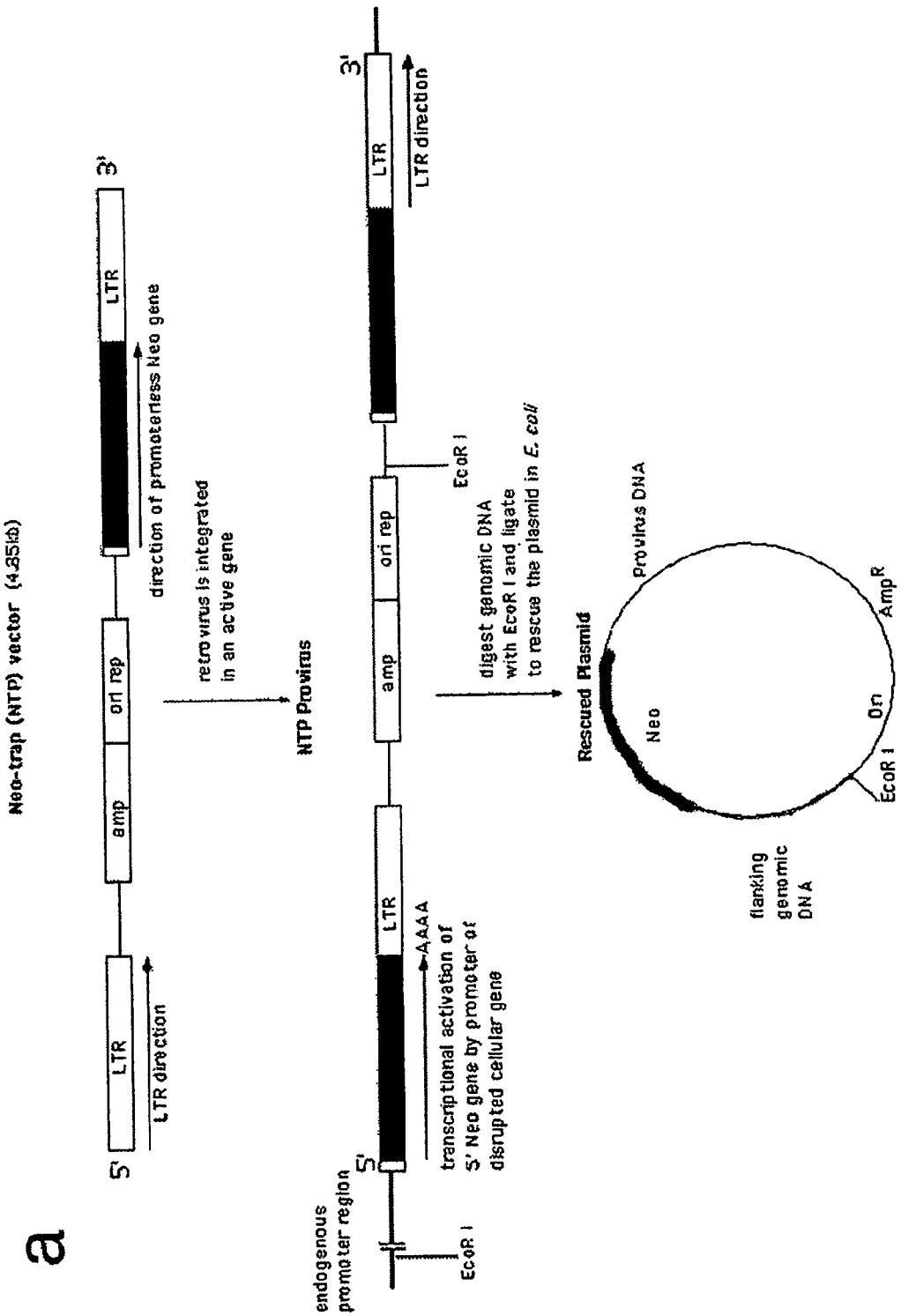
FIG. 6 illustrates a neo-trap vector and neo-resistant cells. (a) Neo-TP retrovital vector carries a promoterless neo gene in its 3' LTR. When a virus is produced in packaging cells, the neo will be duplicated into 5' LTR. When it is used to infect cultured cell, neo-resistant cells will grow out if it is integrated near a gene and activated by an endogenous trapped promoter. (b) Independent clones of neo-resistant cells carrying the Neo-TP activated by a trapped promoter. We have used these cells to produce cloned fish.
Figure 6B:
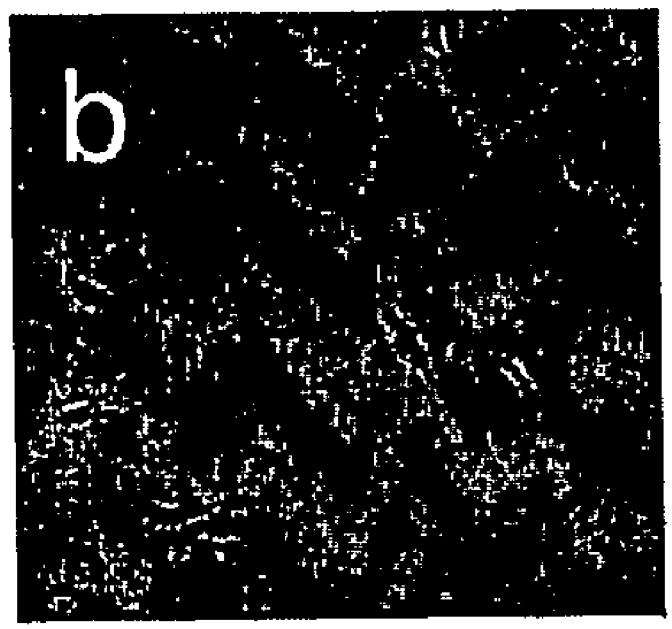
Figure 6B:
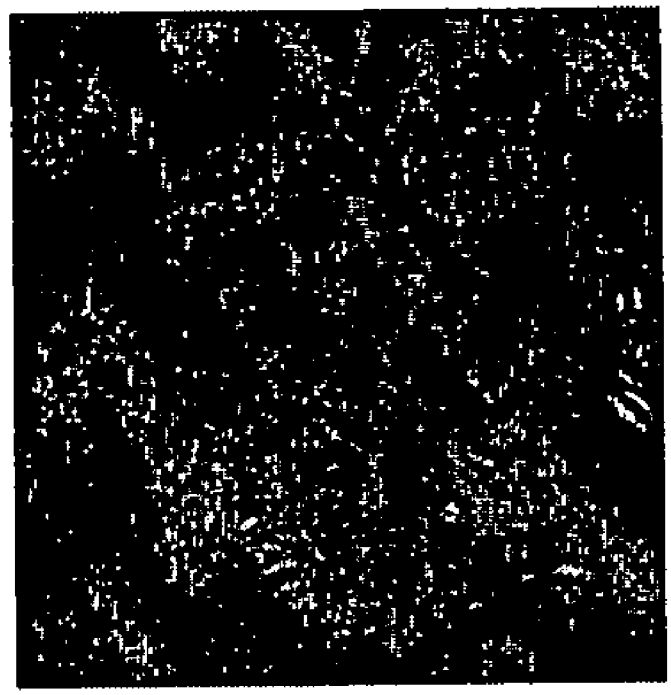

To utilize the cloning technique for characterization of gene functions in zebtafish, we genetically manipulated cultured cells using the gene-trap strategy using two retroviral gene-trap constructs. The first one (SA/GFP-TP), constructed in our laboratory, carries a GFP reporter gene containing a splicing acceptor and an internal neo gene (FIG. 5A). The second one (Neo-TP), lacks a functional promoter and contains a neo gene located in the LTR sequence of a retroviral vector (FIG. 6A) (see, e.g. Hicks et al., (1997) Nat Genet 16, 338-44).

Figures 5B, 5C:
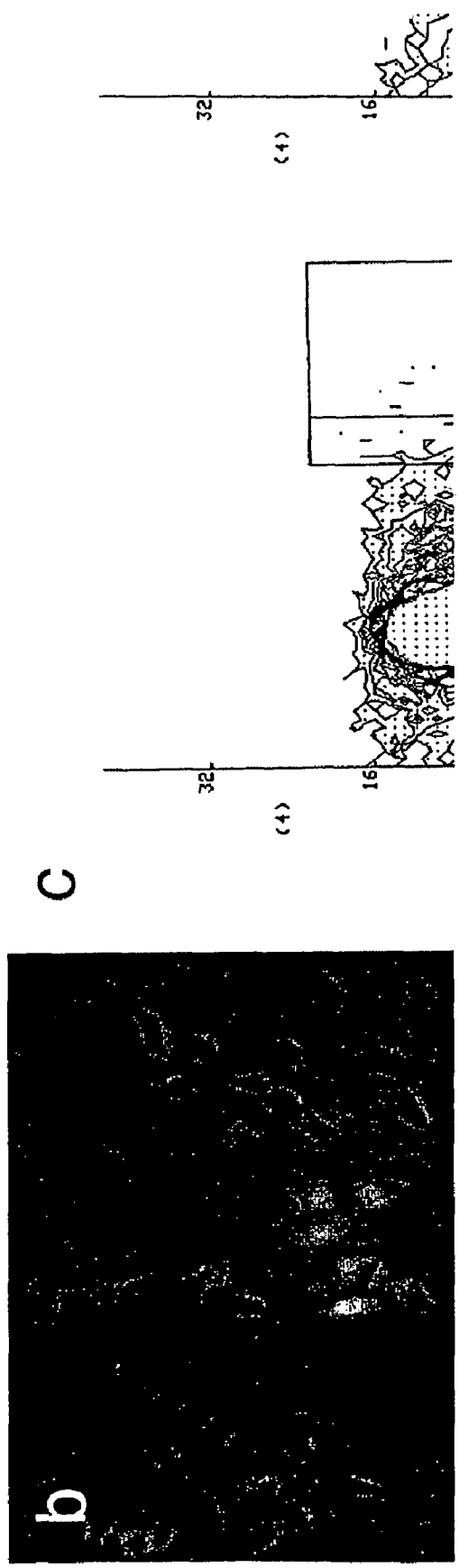

Pseudotyped retrovirus for each gene-trapping construct was generated to infect cultured zebrafish cells that had been successfully used in nuclear transplantation experiments (see, e.g. Lin et al., (1994) Science 265, 666-9). In each case, neo-resistant clones were obtained after drug selection under G418. For SA/GFP-TP, approximately 0.2% cells of the neo-resistant population appeared positive for GFP expression, indicating generation of a GFP fusion protein(s) by splicing (FIG. 5). We are able to directly pick out these cells under a fluorescent microscope for nuclear transfer. We can also select these cells by fluorescence activated cell sorting (FACS) and expand them into individual clones by further culturing single cells.

For Neo-TP, as the neo gene lacks a functional promoter, all of the neo-resistant cells should carry viral insertions downstream of an active promoter (see, e.g. Durick et al., (1999) Genome Res 9, 1019-25). This construct contains an internal ampicillin resistant plasmid DNA fragment with bacterial replication origin, which facilitates the isolation of trapped flanking genomic DNA by a simple plasmid rescue procedure. In order to demonstrate this method, we isolated DNA from the neomycin-resistant fibroblast cells infected by Neo-TP, digested them with EcoR1 restriction enzyme and transformed into bacteria after ligation. This procedure led to the isolation of seven clones carrying flanking cellular DNA with a typical tetroviral integration signature sequence (FIG. 7). These clones contained genomic DNA ranging from 1 kb to 7 kb and sequences of 300-600 bp were obtained from each of the rescued plasmids. Database searching showed that all of them share high homology to zebrafish sequences (Table 3). Interestingly, none of the seven sequences matched any previously known genes but significantly matched to zebrafish ESTs. The relatively short DNA sequences we acquired do not allow us to determine how the structures of the genes have been disrupted. However, with the genome sequencing project actively going on and sequences being annotated, it will be easier in future for us to define the disrupted genes. So far five zebrafish have been cloned from these cells and they will be analyzed for the trapping events and phenotypes once they reach adult stage and progeny axe obtained.

Gene Knockout Approach for Zebrafish Gene Function Studies.

The availability of gene knockout technique in mouse has greatly advanced the ability to analyze gene function in a vertebrate animal. As discussed above, mouse knockout technology relies on ES cells that are not practically available in any other animal systems. Recently, successful knockouts through DNA homologous recombination in non-ES cells followed by animal cloning promised the possibility of performing the same stunt in other systems (see, e.g. Lai et al., (2002) Science 3, 3; McCreath et al., (2000), Nature 405, 1066-9).

Zebrafish, as a superb model for various biological studies, lacks a gene knockout approach to create null mutations by homologous recombination to study specific gene functions. As the instant disclosure demonstrates that long-term cultured cells are able to promote normal zebrafish development after nuclear transfer, there is a high probability that zebrafish "knockouts" through nuclear transfer will be obtained.

As a specific illustration of such methods, we have designed two constructs for homologous recombination in zebrafish cultured cells. The first one is to target zebrafish rag 1 gene and the second one for zebrafish FANCD2. We are currently using these constructs to replace their wild type copies of genes in the cultured cells by DNA homologous recombination. Zebrafish carrying such targeted mutation in these two genes (e.g. by zebrafish cloning using their nuclei as donors) can be readily manipulated according to the methods disclosed herein.

C. Typical Embodiments of the Invention

The invention disclosed herein has a number of embodiments. A preferred embodiment of the invention is a method of making a transgenic fish comprising the steps of introducing an exogenous nucleic acid sequence into the genome of a cultured cell derived from a progenitor fish, transplanting the nucleus of this cell into an egg derived from a parental fish; and then placing the egg generated by this step into conditions suitable for embryonic fish development so that a transgenic fish develops and then hatches.

Preferably the egg derived from the parental fish is enucleated. The disclosure herein that transgenic fish and related fish progeny can be generated using enudeated eggs is surprising in view of art that teaches that it is desirable to use nucleated eggs in such methods because the presence of recipient or host nuclei promotes embryonic development of nuclear transplants (see, e.g. Ju et al., Develop. Growth Differ (2003) 45, 167-174; Ma et al., PNAS (2001) 98(5): 2461-2644). In a preferred embodiment of the invention, the parental fish from which the egg is derived is of the same species as the progenitor fish. Most preferably, the parental fish from which the egg is derived is a clone of the progenitor fish. Alternatively, the parental fish from which the egg is derived is from a different species in the same genera as the as the progenitor fish (see, e.g. Zhu and Sun et al., Cell Research (2000), 10, 17-27).

In a preferred embodiment of the invention, the transgenic fish develops into an adult Optionally the transgenic fish are fertile. In highly preferred embodiments of the invention, the transgenic fish are euploid, i.e. have a diploid number of chromosomes. Alternatively the transgenic fish are aneuploid (e.g. have a triploid or tetraploid number of chromosomes).

In a specific embodiment of this method, the exogenous nucleic acid sequence that is used to generate the transgenic fish includes a gene such as a marker protein that is then expressed in the transgenic fish (e.g. GFP as disclosed in the Examples). In another embodiment of the invention, the exogenous nucleic acid comprises a sequence that regulates gene expression such as the promoter and/or enhancer elements. Alternatively, the transgenic fish is a knock-out transgenic animal having at least one endogenous gene product that is inactivated by the exogenous nucleic acid sequence. In a representative embodiment of the invention, the exogenous nucleic acid sequence is present in a retroviral vector. In another representative embodiment of the invention, the exogenous nucleic acid sequence comprises the *Xenopus* elongation 1 alpha (XeX) promoter.

In highly preferred embodiments of the invention, the cultured cell used to generate the transgenic fish is an embryonic fibroblast derived from an embryo of the progenitor fish. Typically, these embryonic fibroblast cells are generated by obtaining cells from an embryonic fish at a developmental stage as early as the blastula stage to as late as immediately before hatching. Understandably, the cultured cells of the invention exclude blastula cells. Preferably the embryonic sample is taken from somite stage embryos and most preferably from 5-15-somite stage embryos. Cells obtained from the embryonic sample are then disaggregated and placed in in vitro culture and allowed to divide. Cultured embryonic fibroblast cells typically become the predominant cultured cell in in vitro culture. The cultured embryonic fibroblast cells generated from such embryonic samples exhibit a number of typical characteristics including a doubling time that is greater than 24 hours and is approximately 48 hours. In this in vitro culture these cells further exhibit the characteristic fibroblast morphology shown in FIGS. 3A and 3B.

As disclosed herein, fish have been generated from embryonic fibroblast cells in such cultures that have been passaged for more than six months. In the illustrative methods relating to transgenic fish, the embryonic fibroblast cell that is derived from the progenitor fish have been maintained in cell culture for the amount of time sufficient to introduce an exogenous nucleic acid sequence into the genome of the cell and to then identify the cell containing the an exogenous nucleic acid sequence within a plurality of cells comprising the cell having the exogenous nucleic acid sequence and a cell lacking the exogenous nucleic acid sequence. In specific embodiments of the invention, the embryonic fibroblast cell that is derived from the progenitor fish has been maintained in cell culture for an amount of time of at least 1 week, 2 weeks, 3 weeks, 4 weeks, 5 weeks, 6 weeks etc. in one week intervals up to 28 weeks. Optionally the cell has been maintained in culture for a greater period of time. Typically the cells in these cultures have a doubling time that is greater than 24 hours and is approximately 48 hours. In this context, preferably the embryonic fibroblast cell that is derived from the progenitor fish has been maintained in cell culture for an amount of time sufficient for at least 10, 20, 30, 40, 50, 60, 70, 80, 90, 100, 110, 120, 130, 140, 150, 160, 170 or 180 cell divisions. In preferred embodiments of the invention, the chromosomal status of the cultured cells have been examined to confirm that a significant amount (preferably a majority) are euploid prior to the nuclear transplantation step. Optionally, the cell cycle of these cells has been modulated prior to the nuclear transplantation step, preferably by subjecting the cells to serum starvation.

Optionally, the cultured cell derived from the progenitor fish has been frozen prior to the introduction of the exogenous nucleic acid sequence into its genome and/or prior to transplanting the nucleus of this cell into an enucleated egg derived from a parental fish.

Another highly preferred embodiment of the invention is a transgenic fish made according to these methods.

Yet another embodiment of the invention is a method of making a progeny fish comprising obtaining a cell from a progenitor fish, establishing a culture of cells from this progenitor cell, transplanting the nucleus of a cell from this cell culture into an enudeated egg from a parental fish, and then placing the egg generated by this transplantation step into conditions suitable for embryonic fish development so that the progeny fish develops and then hatches. In a preferred embodiment of the invention, the progeny fish that is generated by this method is fertile. In another preferred embodiment of the invention, the progeny fish has a diploid number of chromosomes.

In preferred embodiments of this method, the progeny fish is a transgenic fish. In one embodiment of this method, an exogenous nudeic acid sequence that is used to generate the transgenic fish includes a gene such as a marker protein that is then expressed in the transgenic fish. In another embodiment of the invention, the exogenous nucleic acid that is used to generate the transgenic fish comprises a sequence that regulates gene expression such as the promoter and/or enhancer elements that can be used in gene-trapping methodologies. Alternatively, the transgenic fish is a knock-out transgenic animal having at least one endogenous gene product that is inactivated by the exogenous nucleic acid sequence that is used to generate the transgenic fish.

In highly preferred embodiments of the invention, the cultured cell used to generate the progeny fish is a fibroblast derived from the embryo of the progenitor fish. As disclosed herein, fish have been generated from cells in such cultures that have been passaged for more than six months. Typically, this embryonic fibroblast cell that is derived from the progenitor fish has been maintained in cell culture in an amount of time sufficient to introduce an exogenous nucleic acid sequence into the genome of the cell and to then identify the cell containing the an exogenous nucleic acid sequence within a plurality of cells comprising the cell having the exogenous nucleic acid sequence and a cell lacking the exogenous nucleic acid sequence. Typically this embryonic fibroblast cell that is derived from the progenitor fish has been maintained in cell culture for an amount of time sufficient for at least 10, 20, 30, 40, 50, 60, 70, 80, 90, 100, 110, 120, 130, 140, 150, 160, 170 or 180 cell divisions. Optionally, the cultured cell derived from the progenitor fish has been frozen prior to the introduction of the exogenous nucleic acid sequence into its genome and/or prior to transplanting the nucleus of this cell into an enucleated egg derived from a parental fish.

Another highly preferred embodiment of the invention is a progeny fish made according to these methods.

The methods disclosed herein are applicable to the variety of fish species that have been shown to be amenable to nuclear transplantation. Preferably the progenitor fish are of the species *Danio rerio, Oryzias latipes, Misgurnus anguillicaudatus, Salmo irdeus, Salmo salar, Oreochromis nilotica, Parasilurus asoltus, Mylopharyngodon poceus, Ctnopharyngodon idellus, Hypophthalrmichihys molivtix, Aristichthys nobilis, Cyptinus Carpio* or *Carassius aurantus*. Most preferably the progenitor fish are of the species *Danio rerio*.

D. Advantages of the Invention

Cloning lower vertebrates such as fish and amphibians from long-term cultured cells has been a major challenge due to the dramatic difference between cell cycles of early embryos and cultured cells (see, e.g. M Di Berardino Genomic Potential of Differentiated Cells (Columbia University Press, New York, 1997), p 210). During zebrafish embryonic development it takes approximately 20 minutes to complete each cell cycle for the first 10 cell divisions. However, the same process requires mote than 24 hours in cultured cells.

The disclosure provided herein is the first example where a fish has been successfully cloned using cultured cells. The use of such cultured cells provides significant advantages in a variety of methods, particularly those that involve the introduction of exogenous nucleic acid sequences into the genome of cells (e.g. via a targeting vector such as a retrovirus); and the selection cells possessing the targeted insertion. This disclosure therefore provides a significant advancement in technologies involving the targeted genetic manipulation of fish.

It is worth noting that of those 11 nuclear transplants, 2 individuals were generated from frozen-thawed cells. We also produced additional nuclear transplants using 3 different cell lines that have been frozen over 8 months. The current success rate is approximately 2%, which is equivalent to that of mammalian cloning. As zebrafish produce so many eggs each day, a 2% success rate is sufficient to produce a desirable number of genetically modified individuals. In addition, we have shown that stable clones from these cultured cells can be established and used for DNA transfection (see, e.g. Wang, G et al., Genesis 30, 195-7 (2001)), allowing selection for homologous recombination events.

As an illustration of the power of the methods disclosed herein, we have also infected the long-term cultured cells using a GFP gene-trap virus carrying a splicing acceptor and obtained positive trap events. Consequently, the methods disclosed herein allow fish such as zebrafish to provide genetic tools that are comparable to those offered by mammalian systems.

EXAMPLES

Example 1

Use of Zebrafish in a Typical Embodiment of the Invention

General Methodology

Figure 2:
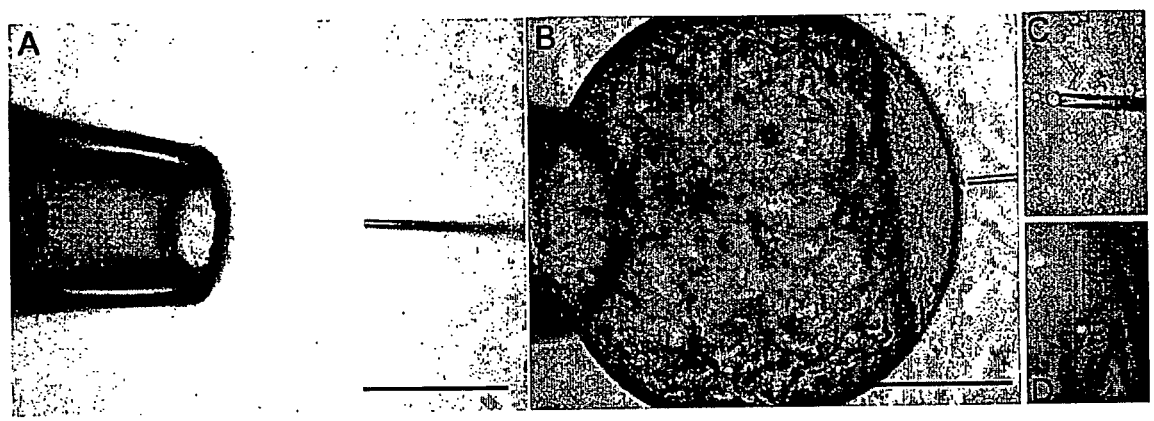
FIG. 2 illustrates enucleation and nuclear transfer in zebrafish. (a) The holding and transfer needles used for nuclear transfer in zebrafish. (b) The transfer needle approaches the second polar body to remove the egg's pronucleus. (c) Picking up a donor cell by the transfer needle. (d) The donor cell nucleus in the transfer needle is green when observed under fluorescent microscope since the donor cells were infected with retrovirus expressing GFP containing a nuclear localization signal. Scale bars=300 µm.

The first step towards cloning the zebrafish is to efficiently remove the pronuclei of the recipient eggs. Matured eggs of teleosts are arrested at the metaphase of the second meiosis. Upon contact with water, the eggs are activated and begin to release their second polar bodies. In zebrafish, the relative size and location of the pronucleus in an unfertilized egg can be revealed using Hoechst 33342 staining (FIG. 1a, 1b). The second polar bodies are visible under a phase contrast microscope after egg activation (FIG. 1c, 1d). The size of the polar body is approximately 8 µm, which appears as a small transparent ball situated immediately above the underlying nucleus. A holding needle with an inner diameter of approximately 260 µm and a transfer needle with the diameter of approximately 10 µm were designed (FIG. 2a) for zebrafish nuclear transfer. A dechorionated egg was held at the tip of the holding needle and positioned so that the animal pole faced the transfer needle (FIG. 2b). Using the second polar body as a reference, the pronucleus was removed by aspirating a small amount of egg cytoplasm just underneath the polar body. It is critical to remove the nucleus in a volume that is as small as possible to avoid compromising the egg's developmental potential. Donor cells for nuclear transfer were picked up by the same transfer needle (FIG. 2c) and ruptured by repeated aspiration with the transfer needle and then transplanted into the cytoplasm of the enucleated egg at the exact position of enucleation. Since we only used GFP positive cells expressing a nuclear localized GFP, the nucleus was visible in the needle under fluorescent light (FIG. 2d).

Primary cells from 5-15-somite stage embryos were first used to test the feasibility of the nuclear transfer procedure. These cells were derived from homozygous transgenic zebrafish expressing the GFP, so that the GFP transgene served as a donor marker to determine if the donor nuclei actually contributed to the developing embryos. We normally performed nuclear transfers in the morning and counted each day's operation as one experimental group. Overall, approximately 20% of experiments yielded developing embryos, most likely due to poor egg quality. In a series of 8 successful nuclear transfer experimental groups involving 67 transplanted eggs, we obtained a total of 20 embryos (30%) that reached blastula stage, 12 embryos (18%) hatched, and 11(16%) of them survived to adulthood (9 females and 2 males, Table 1). All the nuclear transplants expressed GFP, indicating the donor cell nuclei contributed to the development of resulting embryos.

Encouraged by the transplantation results using primary cells as nuclei donors, we continued to determine the cloning competence of long-term cultured somatic cells. 5-15-somite stage embryos were disaggregated and cultured for 8 weeks (FIGS. 3a and 3b). A concentrated stock of pseudotyped retroviral vector containing GFP reporter gene driven by the Xenopus elongation 1 alpha (XeX) promoter was used to infect these cells (see, e.g. Linneyet al., Dev Biol 213, 207-16 (1999)) (FIG. 3c). The titer of the virus was approximately $2 \times 10^7$ colony-forming units per milliliter on these cultured cells. We obtained approximately 20% cells expressing GFP, as determined by FACS analysis and visual inspection under a fluorescent microscope (FIG. 3d). The lower infection rate was chosen because we wished to use cells carrying single viral integration as donors.

Euploid status is a prerequisite for successful nuclear transfer. Therefore, we performed chromosomal analysis to determine the karyotypes of the 12-week-old virus-infected cells. Our data indicate that the majority of cultured cells (77%) contained a normal chromosomal complement (50 chromosomes, 2N). These findings provide evidence that the majority of the long-term cultured cells still possess the desirable karyotype to support normal development of zebrafish after nuclear transfer.

Cloned calves have been successfully produced from fetal fibroblasts without serum starvation (see, e.g. Cibelli, J B et al., Science 280, 1256-8 (1998)). However, more reports are in favor of including serum starvation in nuclear transfer experiments. Studies in sheep suggest that arrest in G0 by serum starvation is important, allowing donor somatic nuclei to better support development of embryos (see, e.g. Wilmut et al., Nature 385, 810-3 (1997); Wilmut et al., Nature 385, 810-3 (1997)). Additionally, Kasinathan et al. has showed that nuclei from G1 cells are important for supporting late fetal development (see, e.g. Kasinathan et al., Nat Biotechnol 19, 1176-8 (2001)). In our case, we selected to include a starvation step because a starvation step appear to push more cells into G0+G1 that should be more beneficial in zebrafish nuclear transfer.

The virus-infected cells at 12 week-old were tested for the effect of serum starvation on DNA content. FIG. 3f and 3g show representative histograms of cell cycle by FACS depicting cells from serum-starved and none-serum-starved cells. In the none-starved cells (FIG. 3f), 59% was at G0+G1 stage whereas serum starvation for 4 days (FIG. 3g) increased G0+G1 stage cells to 80%. Based on this observation, a 4-day serum-starvation was applied to all donor cells used for nuclear transfer.

Figure 4:
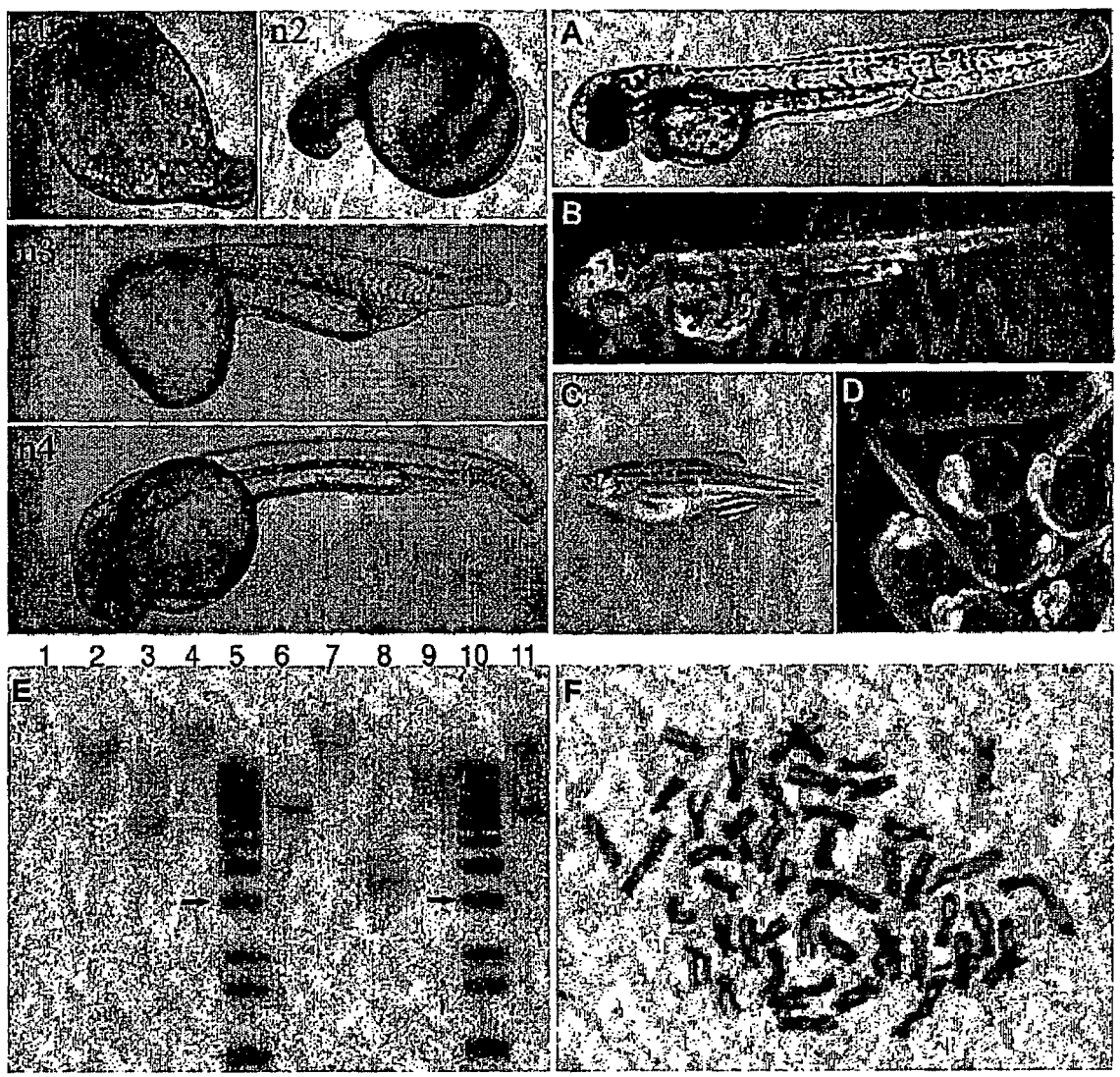
FIG. 4 illustrates transgenic zebrafish embryos produced by nuclear transfer (n1-n4). Various phenotypes of embryos obtained by nuclear transfer. (a and b) Expression of GFP in a F0 embryo (bright field and fluorescent image). (c) Adult zebrafish produced by nuclear transfer. (d) GFP expression in the F1 offspring from the F0 fish in (b). Only GFP-positive embryos were photographed, which were approximately 50% of the total progeny. (e) Southern blot analysis of integration patterns of cloned zebrafish carrying viral insertions. The genomic DNA was digested with HpaI, which does not cut the proviral DNA. Presumably, HpaI will only cut the flanking genomic DNA, which should be unique for each independent integration site. The entire proviral DNA is approximately 3.2 kb and all of the hybridization bands appear bigger than 3.2 kb. Lane 1 is a negative control using wild type zebrafish Lane 2, 3, 4, 6, 7, 8, 9, and 11 are different lines of the cloned zebrafish. Lane 5 and 9 are molecular markets (arrows indicate 3 kb). Please note that lane 11 has two hybridization bands, suggesting that the donor cell carries two insertions. (f) Metaphase chromosomes from a F2 embryo from a nuclear transplant fish. The number of chromosomes are 50.

Cells used for nuclear transfer were cultured for a minimum of 12 weeks and subjected to serum starvation. As experiments went on, the oldest cells in the experiments were approximately 26 weeks old. For those experiments that produced developing nuclear transplants, normal individuals as well as embryos exhibited various degrees of abnormality were also obtained (FIG. 4 n1-n4). Again, more than 80% of experiments failed to produce developing embryos. From 10 experimental groups that produced embryos that went through cell cleavages, a total of 34 embryos (36%) reached the blastula stage, 15 embryos (16%) in 6 groups hatched, and 11 (12%) of these embryos reached adulthood (Table 2). The 11 adults represent approximately 2% of total embryos operated.

All of the transplanted embryos we obtained expressed GFP, confirming that donor cells contributed to their development As shown in FIGS. 4a and 4b, the transgenic embryo produced by cloning has a ubiquitous expression pattern reminiscent of that of retroviral XeX-GFP transgenic zebrafish (see, e.g. Linney et al., Dev Biol 213, 207-16 (1999)). Adult zebrafish produced by nuclear transfer appear indistinguishable from normal wild type zebrafish FIG. 4c). We did not notice any obvious difference in their growth rate, aging process and fertility.

Of those normal individuals, 9 adults produced offspring after mating with wild-type fish. The offspring of these transgenic lines continued to express GFP (FIG. 4d) and the expression patterns were the same as those of the nuclear transplants throughout the embryonic development The GFP donor marker gene was transmitted to the subsequent generations following a Mendelian fashion. Homozygous and fertile transgenic zebrafish expressing GFP were established at the F2 generation. These data provide evidence that the viral insertions are stably integrated into the zebrafish genome.

Because we used individual non-clonal donor cells that were infected with virus at relatively low frequency, each resultant nuclear transplant should contain a unique retroviral insertion. To determine this, we analyzed integration sites in the 8 cloned fish lines by Southern blot. As shown in FIG. 4e, each line has a junction fragment that is different from others, confirming that they were derived from different donor cells. We have also examined the karyotypes of F2 embryos at 12 hours post fertilization and no detectable chromosoral abnormalities were observed (N=50, FIG. 4f). Together, these data support a conclusion that we have produced diploid and fertile transgenic zebrafish by nuclear transfer. Interestingly, we noticed that majority of the nuclear transplants were female. However, it remains to be determined if this represents a statistically significant fact.

Media for Nuclear Transfer

The eggs were held in Hank's saline solution (0.137 M NaCl, 5.4 mM KCl, 0.025 mM $Na_2HPO_4$, 0.44 mM $KH_2PO_4$, 1.3 mM $CaCl_2$, 1.0 mM $MgSO_4$, 4.2 mM $NaHCO_3$) supplemented with 1.5% bovine serum albumin (BSA, Sigma fraction V) as described in the art (see, e.g. Sakai et al., Mol Mar Biol Biotechnol 6, 84-87 (1997)). This working media was kept at 4° C. until nuclear transfer.

Preparation of Recipient Eggs.

The day before nuclear transfer, individual wild type female zebrafish were placed in mating cages with males, which were separated from each other by a divider. After initiation of the light cycle, the female was placed together with 1 or 2 males by removing the divider. As soon as breeding activity commenced, the female was removed from the mating cage and squeezed to obtain unfertilized eggs. Eggs of good quality are slightly granular and yellowish in color whereas immature eggs appear whitish or withered. The best eggs also appear intact and smooth on the yolk surface. The eggs were immediately placed in Holtfreter's solution and dechorionated with pronase. These eggs can be used as recipients up to 1 hour after activation.

To visualize the nuclei from fixed unfertilized eggs, Hoechst 33342 staining was performed. Briefly, the unfertilized eggs were fixed for 1 hour at room temperature in 4% paraformaldehyde, stained for 10 min in Hoechst 33342 (1 mg/ml) and washed for 10 times in PBS. The stained eggs were visualized under UV light using a fluorescent Zeiss microscope.

Preparation of Donor Cells.

Primary cells were collected from 5-15 somite embryos and immediately used for nuclear transfer. Briefly, the embryos were dissociated in trypsin/EDTA (0.2% trypsin/1 mM EDTA in PBS), collected by centrifugation, washed and dissociated cells were kept on ice in Dulbecco's modified Eagle's medium DMEM) until nuclear transfer. Normally, the cells will be used for nuclear transfer less than 60 minutes after preparation.

To establish long-term cultured cells for nuclear transfer, primary cells were first cultured at 28-29° C. with 5% $CO_2$ in DMEM which was supplemented with 15% heat-inactivated fetal bovine serum (FBS), bovine basic fibroblast growth factor (50 ng/ml, Sigma), 3 mM L-glutamin, 5% zebrafish embryo extract, 100 units/ml penicillin and 100 µg/ml streptomycin. These primary cells were passed over 8 weeks (approximately 13 passages) and established as long-term cultured cell. They were then infected using a pseudotyped vital vector carrying the GFP gene driven by the XeX promoter. Infected cells, named Ezfb-RIGFP, were cultured for an additional 4 weeks prior to nuclear transfer. Virus-infected donor cells (22 passages) were subjected to serum starvation (0.5% FBS) for 3-4 days after reaching confluence. These cells were dissociated in trypsin/EDTA, washed, collected by centrifugation, and suspended in the 0.5% FBS-medium. Cells in suspension were placed on ice until nuclear transfer.

Cell Cycle Analysis

Cell cycle analysis was performed as described. Briefly, cell cultures were grown to confluence under either serum-starved (0.5% FBS) or non-starved (15% FBS) conditions. Cells were trypsinized, washed with DMEM, and resuspended to a concentration of $1 \times 10^6$ cells/ml in ice-cold ethanol. Cells were fixed for at least 1 hour in ethanol at 4° C. For nuclear staining, a 1 ml aliquot ($1 \times 10^6$ cells/ml) was resuspended in PBS and passed through a 25G5/8 syringe. Next, 2 ml of RNase A (10 mg/ml, Sigma) and 10 ml of propidium iodide (5 mg/ml, Sigma) were added. Cells were incubated for 30 minutes at room temperature in the dark and then analyzed by fluorescence-activated cell sorting (FACS).

Nuclear Transfer.

To remove the egg pronudei, recipient eggs were placed in a drop of Hank's solution (about 100 μl) containing 1.5% BSA and then covered with mineral oil (Sigma). After activation, the cytoplasm of the fish egg coalesces, moves toward the animal pole, and forms the blastodisc. The blastodisc of the zebrafish takes about 12 minutes to form at 24° C. and after 40 min it becomes a full-sized one-cell egg. We normally carry out nuclear transfer prior to the completion of blastodisc formation. Each dechorionated egg was oriented using the holding/injection needle to determine the position of pronucleus, which is located at the animal pole just underneath the egg surface against the second polar body, which could be identified as a transparent ball of approximately 8 μm diameter. The nucleus was sucked out from the egg with a fine glass needle by aspirating a small amount of cytoplasm just underneath the polar body.

All nuclear transfers were performed using either an Eppendorf microinjection system (Model 5171/5246) with the Nikon TE300 microscope or a Narishige system (NT-188NE) with the Axiovert 200 microscope. Individual cells expressing GFP identified using a fluorescein isothiocyanate filter on an inverted fluorescent microscope were used as donors. Donor cells were ruptured by aspirating into the transfer needle, which has an inner diameter smaller than the cell (~12 μm). Next, they were transplanted into the cytoplasm of the enucleated eggs at the animal pole. Each of the nuclear transplants was transferred into a single well of a 24-well-plastic plate filled with Holtfreter's solution. Nuclear transplants were cultured in Holtfreter's solution at 28° C. until hatching. Hatched embryos were then placed into fish water and reared to the adult stage.

Chromosome Analysis.

To examine the ploidy status of the cultured somatic donor cells (12 week-old) and $F_1$ progeny from nuclear transplant fish, chromosome numbers were determined by using standard method for chromosome preparation. Briefly, the cells were treated with hypotonic KCl (0.075 M) for 15 minutes at 37° C., fixed in acetic acid/methanol (vol/vol=1: 3), and drops of cell suspension were spread on dean microscopic slides. The chromosomes were stained with 0.4% Giemsa for 10 min at room temperature. The numbers of well-spread chromosomes within a dear cell boundary were counted under a light microscope at 1,000× magnification under oil. At least 20 metaphase spreads were counted from each preparation.

Southern Blotting Analysis.

The genomic DNA from each fish was digested with restriction enzyme HpaI, separated by electrophoresis and blotted on nylon membrane. A 2.1 kb fragment of the proviral DNA was labeled with $P^{32}$ and hybridized to the membrane using the Stratagene QuickHyb solution. To reveal the sizes of the hybridization bands, 1 kb marker DNA consisting of about 1% of the proviral DNA probe, was also labeled and used for hybridization.

Throughout this application, various publications are referenced, for example, to provide examples of the state of the art (e.g. U.S. Pat. No. 6,380,458). The disclosures of these publications are hereby incorporated by reference herein in their entireties. In order to clearly illustrate the state of the art, certain standard terms and methodologies from these incorporated publications are explicitly disclosed herein.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE 1

Nuclear transplants generated using primary embryonic cells

| experimental group | Eggs operated | No. of individuals | | |
|---|---|---|---|---|
| | | Blastula | Hatched | Adult |
| N1 | 9 | 3 | 2 | 2 |
| N2 | 9 | 4 | 2 | 2 |
| N3 | 8 | 2 | 2 | 1 |
| N4 | 9 | 2 | 1 | 1 |
| N5 | 7 | 3 | 1 | 1 |
| N6 | 8 | 2 | 2 | 2 |
| N7 | 8 | 2 | 1 | 1 |
| N8 | 9 | 2 | 1 | 1 |
| Total | 67 | 20(30) | 12(18) | 11(16) |

* Numbers in parentheses represent the percentage of the total number of transplants from 8 experiments that yielded developing embryos. This table only lists those operations that produced nuclear transplants that developed to blastula or later stages. Other 20 experiments involving approximately 170 eggs yielded no developing embryos.

TABLE 2

Nuclear transplants generated using long-term cultured fibroblast cells

| Experimental groups | Eggs operated | No. of individuals | | |
|---|---|---|---|---|
| | | Blastula | Hatched | Adult |
| N1 | 15 | 5(33) | 4(27) | 2(13) |
| N2 | 14 | 7(50) | 3(21) | 2(14) |
| N3 | 7 | 5(71) | 2(29) | 1(14) |
| N4 | 9 | 3(33) | 2(22) | 2(22) |
| N5 | 9 | 3(33) | 2(22) | 2(22) |
| N6 | 8 | 2(25) | 0(0) | 0(0) |
| N7 | 9 | 1(11) | 0(0) | 0(0) |
| N8 | 6 | 2(33) | 0(0) | 0(0) |
| N9 | 9 | 3(33) | 0(0) | 0(0) |
| N10 | 8 | 3(38) | 2(25) | 2(25) |
| Total | 94 | 34(36) | 15(16) | 11(12) |

* Numbers in parentheses represent the percentage of the total number of transplants. This table only lists those operations that produced nuclear transplants that developed to blastula or later stages. Other 50 experiments involving approximately 450 eggs yielded no developing embryos.

TABLE 3

BLASTN search results of zebrafish DNA sequences identified by Neo-TP selection

| Trapped clones | Species | Sequence ID/ Scores |
|---|---|---|
| Trap1 | zebrafish | AL590146/5e-42 |
| Trap11 | zebrafish | AL772279/2e-26 |
| Trap19 | zebrafish | AL590151/2e-69 |
| Trap31 | zebrafish | AL596027/6e-91 |
| Trap36 | zebrafish | AL732436/4e-18 |
| TrapA3 | zebrafish | AL807389/5e-24 |
| TrapA4 | zebrafish | AL590148/2e-38 |

The invention claimed is:

1. A method of making a diploid transgenic oviparous teleost fish comprising:
   (a) introducing an exogenous nucleic acid sequence into the genome of a cultured embryonic fibroblast cell derived from a progenitor *Danio rerio* embryo;
   (b) transplanting the nucleus of the cell of step (a) into an enucleated egg derived from a parental fish, wherein the parental fish is of the same species as the progenitor if fertile progeny are desired; and
   (c) culturing the resultant embryo in conditions suitable for embryonic fish development so that a diploid transgenic oviparous teleost fish is made.

2. The method of claim 1, wherein the transgenic fish has at least one exogenous gene product expressed therein that is encoded by the exogenous nucleic acid sequence.

3. The method of claim 1, wherein the exogenous nucleic acid sequence comprises a promoter element and an enhancer element.

4. The method of claim 1, wherein the parental fish is of the same species as the progenitor fish and the resulting transgenic fish is fertile.

5. The method of claim 1, wherein the cultured embryonic fibroblast cell derived from the *Danio rerio* embryo has been maintained in cell culture for an amount of time sufficient for at least 10, 20, 30, 40, 50, 60, 70, 80, 90, 100, 110, 120, 130, 140, 150, 160, 170 or 180 cell divisions prior to transplanting the nucleus of the embryonic fibroblast into an enucleared egg.

6. The method of claim 1, wherein the cultured cell derived from the progenitor fish has been frozen prior to step (a) or step (b).

7. A method of making a progeny *Danio rerio* comprising:
   (a) obtaining an embryonic fibroblast cell from a progenitor *Danio rerio* embryo,
   (b) maintaining the cell in in vitro culture,
   (c) transplanting the nucleus of the cell of step (b) into an enucleated egg from a parental *Danio rerio* and,
   (d) culturing the resultant embryo in conditions suitable for embryonic fish development such that the progeny *Danio rerio* is made.

8. The method of claim 7, wherein the progeny fish is diploid.

9. The method of claim 7, wherein the progeny fish is a transgenic fish.

10. The method of claim 9, wherein the transgenic fish expresses at least one exogenous gene product encoded by a transgene.

11. The method of claim 9, wherein the transgenic fish has at least one endogenous gene product that is inactivated by the transgene.

12. The method of claim 9, wherein the transgenic fish comprises an exogenously introduced promoter element and enhancer element.

13. The method of claim 7, wherein the cell is maintained in in vitro culture an amount of time sufficient to:
   (i) introduce an exogenous nucleic acid sequence into the genome of the cell; and
   (ii) identify the cell containing the an exogenous nucleic acid sequence within a plurality of cells comprising the cell having the exogenous nucleic acid sequence and a cell lacking the exogenous nucleic acid sequence.

14. The method of claim 7, wherein the cell is maintained in culture an amount of time sufficient for at least 40, 50, 60, 70, 80, 90, 100, 110, 120, 130, 140, 150, 160, 170 or 180 cell divisions.

* * * * *

UNITED STATES PATENT AND TRADEMARK OFFICE
CERTIFICATE OF CORRECTION

PATENT NO. : 7,332,647 B2
APPLICATION NO. : 10/517880
DATED : February 19, 2008
INVENTOR(S) : Shuo I. Lin Page 1 of 1

It is certified that error appears in the above-identified patent and that said Letters Patent is hereby corrected as shown below:

Column 1

Lines 13-15, under STATEMENT OF GOVERNMENT SUPPORT, please delete "The present invention was made with Government support by a National Institutes of Health Grant R01 RR13227. The Government has certain rights in this invention." and replace with --The present invention was made with Government support by a National Institutes of Health Grants DK052355, HD039121, and RR013227. The Government has certain rights in this invention.--

Signed and Sealed this

Thirty-first Day of March, 2009

JOHN DOLL
*Acting Director of the United States Patent and Trademark Office*